US011476000B2

(12) United States Patent
Burton et al.

(10) Patent No.: US 11,476,000 B2
(45) Date of Patent: *Oct. 18, 2022

(54) METHODS AND SYSTEMS USING MATHEMATICAL ANALYSIS AND MACHINE LEARNING TO DIAGNOSE DISEASE

(71) Applicant: Analytics For Life Inc., Toronto (CA)

(72) Inventors: Timothy Burton, Ottawa (CA); Shyamlal Ramchandani, Kingston (CA); Sunny Gupta, Amherstview (CA)

(73) Assignee: Analytics For Life Inc., Toronto (CA)

( * ) Notice: Subject to any disclaimer, the term of this patent is extended or adjusted under 35 U.S.C. 154(b) by 207 days.

This patent is subject to a terminal disclaimer.

(21) Appl. No.: 16/889,478

(22) Filed: Jun. 1, 2020

(65) Prior Publication Data

US 2020/0335217 A1    Oct. 22, 2020

Related U.S. Application Data

(63) Continuation of application No. 15/911,881, filed on Mar. 5, 2018, now Pat. No. 10,672,518, which is a
(Continued)

(51) Int. Cl.
*A61B 5/00* (2006.01)
*G16H 50/20* (2018.01)
(Continued)

(52) U.S. Cl.
CPC .............. *G16H 50/20* (2018.01); *A61B 5/02* (2013.01); *A61B 5/24* (2021.01); *A61B 5/283* (2021.01);
(Continued)

(58) Field of Classification Search
CPC combination set(s) only.
See application file for complete search history.

(56) References Cited

U.S. PATENT DOCUMENTS 5,029,082 A    7/1991   Shen et al.
5,769,074 A    6/1998   Barnhill et al.
(Continued)

FOREIGN PATENT DOCUMENTS

CN    101911083    12/2010
CN    103610457    3/2014
(Continued)

OTHER PUBLICATIONS

Edelsbrunner, H., et al., "Three-Dimensional Alpha Shapes," ACM Transactions on Graphics, vol. 13, No. 1, 1994, pp. 43-72.
(Continued)

*Primary Examiner* — George Manuel
(74) *Attorney, Agent, or Firm* — Meunier Carlin & Curfman LLC

(57) ABSTRACT

Exemplified method and system facilitates monitoring and/or evaluation of disease or physiological state using mathematical analysis and machine learning analysis of a biopotential signal collected from a single electrode. The exemplified method and system creates, from data of a singularly measured biopotential signal, via a mathematical operation (i.e., via numeric fractional derivative calculation of the signal in the frequency domain), one or more mathematically-derived biopotential signals (e.g., virtual biopotential signals) that is used in combination with the measured biopotential signals to generate a multi-dimensional phase-space representation of the body (e.g., the heart). By mathematically modulating (e.g., by expanding or contracting) portions of a given biopotential signal, in the frequency domain, the numeric-based operation gives emphasis or de-emphasis to certain measured frequencies of the biopo-
(Continued)

tential signals, which, when coupled with machine learning, facilitates improved diagnostics of certain pathologies.

20 Claims, 12 Drawing Sheets

Related U.S. Application Data continuation of application No. 15/192,639, filed on Jun. 24, 2016, now Pat. No. 9,910,964.

(60) Provisional application No. 62/184,796, filed on Jun. 25, 2015.

(51) Int. Cl.
| | | |
|---|---|---|
| A61B 5/24 | (2021.01) | |
| A61B 5/283 | (2021.01) | |
| A61B 5/316 | (2021.01) | |
| A61B 5/02 | (2006.01) | |
| A61B 5/341 | (2021.01) | |

(52) U.S. Cl.
CPC ............ *A61B 5/316* (2021.01); *A61B 5/4848* (2013.01); *A61B 5/725* (2013.01); *A61B 5/726* (2013.01); *A61B 5/7257* (2013.01); *A61B 5/7264* (2013.01); *A61B 5/7275* (2013.01); *A61B 5/7278* (2013.01); *A61B 5/341* (2021.01); *A61B 5/681* (2013.01); *A61B 5/6801* (2013.01); *A61B 5/6823* (2013.01); *A61B 5/6824* (2013.01); *A61B 5/7203* (2013.01); *A61B 5/7267* (2013.01)

(56) References Cited

U.S. PATENT DOCUMENTS

| | | | |
|---|---|---|---|
| 6,310,968 | B1 | 10/2001 | Hawkins et al. |
| 6,522,712 | B1 | 2/2003 | Yavuz et al. |
| 6,709,399 | B1 | 3/2004 | Shen et al. |
| 7,733,224 | B2 | 6/2010 | Tran |
| 8,157,742 | B2 | 4/2012 | Taylor et al. |
| 8,923,958 | B2 | 12/2014 | Gupta et al. |
| 9,131,864 | B2 | 9/2015 | Korenberg |
| 9,289,150 | B1 | 3/2016 | Gupta et al. |
| 9,408,543 | B1 | 8/2016 | Gupta et al. |
| 9,597,021 | B1 | 3/2017 | Gupta et al. |
| 9,655,536 | B2 | 5/2017 | Gupta et al. |
| 9,737,229 | B1 | 8/2017 | Gupta et al. |
| 9,955,883 | B2 | 5/2018 | Gupta et al. |
| 9,968,275 | B2 | 5/2018 | Gupta et al. |
| 2002/0156385 | A1 | 10/2002 | Feng et al. |
| 2004/0081270 | A1 | 4/2004 | Heuscher |
| 2004/0230105 | A1 | 11/2004 | Geva et al. |
| 2007/0086563 | A1 | 4/2007 | Bruder |
| 2007/0276270 | A1 | 11/2007 | Tran |
| 2009/0177102 | A1 | 7/2009 | Schneider et al. |
| 2009/0242776 | A1 | 10/2009 | Kobashi et al. |
| 2009/0274375 | A1 | 11/2009 | Kavanau et al. |
| 2011/0105897 | A1 | 5/2011 | Kornblau et al. |
| 2011/0245675 | A1 | 10/2011 | Yoshida et al. |
| 2012/0232853 | A1 | 9/2012 | Voigt et al. |
| 2012/0321759 | A1 | 12/2012 | Marinkovich et al. |
| 2013/0096394 | A1 | 4/2013 | Gupta et al. |
| 2013/0172691 | A1 | 7/2013 | Tran |
| 2014/0029829 | A1 | 1/2014 | Jiang et al. |
| 2014/0309707 | A1 | 10/2014 | Marculescu et al. |
| 2015/0133803 | A1 | 5/2015 | Gupta et al. |
| 2015/0216426 | A1 | 8/2015 | Burton et al. |
| 2015/0250450 | A1 | 9/2015 | Thomas et al. |
| 2015/0297161 | A1 | 10/2015 | Grass et al. |
| 2015/0359601 | A1 | 12/2015 | Sauer et al. |
| 2016/0191887 | A1* | 6/2016 | Casas .............. G06T 19/006 348/47 |
| 2016/0364861 | A1 | 12/2016 | Taylor et al. |
| 2017/0045600 | A1 | 2/2017 | Hsiao et al. |
| 2017/0119272 | A1 | 5/2017 | Gupta et al. |
| 2018/0000371 | A1 | 1/2018 | Gupta et al. |
| 2018/0033991 | A1 | 2/2018 | Yamashita et al. |
| 2018/0078146 | A1 | 3/2018 | Shadforth et al. |
| 2018/0249960 | A1 | 9/2018 | Gupta et al. |
| 2019/0200893 | A1 | 7/2019 | Grouchy et al. |
| 2019/0214137 | A1 | 7/2019 | Gupta et al. |

FOREIGN PATENT DOCUMENTS

| | | |
|---|---|---|
| CN | 103886184 | 6/2014 |
| CN | 103954697 | 7/2014 |
| CN | 103054572 | 4/2015 |
| JP | 2014/171660 | 9/2014 |
| WO | 2007/041807 | 4/2007 |

OTHER PUBLICATIONS

Feeny, B.F., et al., "Fractional Derivatives Applied to Phase-Space Reconstructions," Nonlinear Dynamics, vol. 38, 2004, pp. 85-99.

Goutas, A., et al., "Digital fractional order differentiation-based algorithm for P and T-waves detection and delineation," ITBM-RBM, vol. 26, Issue 2, 2005, pp. 127-132.

Karvounis, E.C., et al., "Detection of Fetal Heart Rate Through 3-D Phase Space Analysis from Multivariate Abdominal Recordings," IEEE Transaction on Biomedical Engineering, vol. 56, No. 5, 2009, 13 pages.

Mallat, S.G., et al., "Matching Pursuits with Time-Frequency Dictionaries," IEEE Transactions on Signal Processing, vol. 41, No. 12, 1993, pp. 3397-2415.

MATLAB™ (Mathworks: Natick, MA) Wavelet Toolbox™ User's Guide, 1997, 736 pages.

Matteo, T., et al., "Scaling behaviors in differently developed markets," Physica A, vol. 324, 2003, pp. 183-188.

Saptarshi, D., et al., "Fractional dynamical model for the generation of ECG like signals from filtered coupled Van-der Pol oscillators," Computer Methods and Programs in Biomedicine, vol. 112, No. 3, 2013, pp. 490-507.

Tseng, C-C., et al., "Computation of fractional derivatives using Fourier transform and digital FIR differentiatior," Signal Processing, vol. 80, 2000, pp. 151-159.

Wang, J., et al., "Fractional zero-phase filtering based on the Riemann-Liouville integral," Signal Processing, vol. 98, 2013, pp. 150-157.

Weston, et al., "Co-variation in Frequency and Severity of Cardiovascular and Skeletal Defects in Sprague-Dawley Rats After Maternal Administration of Dimethadione, the N-demethylated Metabolite of Trimethadione," Birth Defects Research (Part B), vol. 92, 2011, pp. 206-215.

Search Report, dated Apr. 3, 2020, received in connection with corresponding CN Patent Application No. 201680037157.9 (English translation).

Supplementary Search Report, dated Sep. 28, 2018, received in connection with corresponding EP Patent Application No. 16813834.5.

First Office Action, dated Jun. 19, 2018, received in connection with corresponding JP Patent Application No. 2017-567215 (English translation).

Office Action dated Feb. 15, 2018, received in connection with corresponding CA Patent Application No. 2,990,367.

International Search Report and Written Opinion, dated Oct. 5, 2016, received in connection with corresponding International Patent Application No. PCT/IB2016/053797.

Collins, F., et al., "A New Initiative in Precision Medicine," The New England Journal of Medicine, vol. 372, No. 9, 2015, pp. 793-795.

Fihn, S. D., et al., "2012 ACCF/AHA/ACP/AATS/PCNA/SCAI/STS Guideline for the Diagnosis and Management of Patients With Stable Ischemic Heart Disease," Journal of the American College of Cardiology, 2012, vol. 60, pp. e44-e164.

(56) References Cited

OTHER PUBLICATIONS

Freund, Y., et al., "A decision-theoretic generalization of on-line learning and an application to boosting," Proceedings of the Second European Conference on Computational Learning Theory, 1995, 15 pages.

Krittanawong, C., et al., Artificial Intelligence in Precision Cardiovascular Medicine, Journal of the American College of Cardiology, vol. 69, 2017, pp. 2657-2664.

Louridas, G., et al., Impact of Chaos in the Progression of Heart Failure, International Journal of Applied Science and Technology, vol. 2, No. 7, 2012, pp. 24-30.

Magin, R. L., et al., "Modeling the Cardiac Tissue Electrode Interface Using Fractional Calculus," Journal of Vibration and Control, vol. 14, Nos. 9-10, 2008, pp. 1431-1442.

Matcharashvili, T., et al., "Identification of Complex Processes Based on Analysis of Phase Space Structures," Imaging for Detection and Identification, NATO Security through Science Series, 2007, pp. 207-242.

Narula, S., et al., "Machine-Learning Algorithms to Automate Morphological and Functional Assessments in 2D Echocardiography," Journal of the American College of Cardiology, vol. 68, 2016, pp. 2287-2295.

Oakden-Rayner, L., et al., "Precision Radiology: Predicting longevity using feature engineering and deep learning methods in a radiomics framework," Scientific Reports, vol. 7, No. 1648, 2017, 13 pages.

Ruigómez, A., et al., "Chest pain in general practice: incidence, comorbidity and mortality," Family Practice, 2006, vol. 23, pp. 167-174.

Stuckey, T., "Noninvasive Detection of Coronary Artery Disease Using Resting Phase Signals and Advanced Machine Learning," CONE Health, LeBauer-Brodie Center for Cardiovascular Research Foundation, TCT, 2017, 14 pages.

Xiong, G., et al., "Myocardial Perfusion Analysis in Cardiac Computed Tomography Angiographic Images at Rest," Medical Image Analysis, vol. 24, vol. 1, 2016, 39 pages.

Zimmerman, M. W., et al., "A Reconstructed Phase Space Approach for Distinguishing Ischemic from Non-Ischemic ST Changes using Holter ECG Data," Computers in Cardiology, 2003, vol. 30, pp. 243-246.

\* cited by examiner

METHODS AND SYSTEMS USING MATHEMATICAL ANALYSIS AND MACHINE LEARNING TO DIAGNOSE DISEASE

CROSS REFERENCE TO RELATED APPLICATIONS

This is a continuation application of U.S. patent application Ser. No. 15/911,881, filed Mar. 5, 2018, titled "Method and System Using Mathematical Analysis and Machine Learning to Diagnose Disease," now U.S. Pat. No. 10,672,518, which is a continuation application of U.S. patent application Ser. No. 15/192,639, filed Jun. 24, 2016, titled "Method and System Using Mathematical Analysis and Machine Learning to Diagnose Disease," now U.S. Pat. No. 9,910,964, which claims priority to, and the benefit of, U.S. Provisional Application No. 62/184,796, filed Jun. 25, 2015, titled "Latent Teratogen-Induced Heart Deficits Are Unmasked Postnatally with Mathematical Analysis and Machine Learning on ECG Signals," the content of which is incorporated by reference herein in its entirety.

TECHNICAL FIELD

The present disclosure relates to methods and systems to diagnose cardiac pathologies via mathematical and machine learning analysis on biopotential signals.

BACKGROUND

Congenital heart defects (CHDs) are the most common birth anomaly, with ventricular septal defects (VSDs) being the most prevalent category of congenital heart defects (CHDs). Clinically, about 80% of ventricular septal defects (VSDs) resolve spontaneously within the first year, but little is known about the long-term consequences of these resolved VSDs on postnatal heart function.

What are needed are devices, systems and methods that overcome challenges in the present art, some of which are described above.

SUMMARY

Exemplified method and system facilitates monitoring and/or evaluation of disease or physiological state using mathematical analysis and machine learning analysis of a biopotential signal collected from a single electrode. The exemplified method and system creates, from data of a singularly measured biopotential signal, via a mathematical operation (i.e., via fractional derivative calculation), one or more mathematically-derived biopotential signals (e.g., virtual biopotential signals) that is used in combination with the measured biopotential signals to generate a multi-dimensional phase-space representation of the body (e.g., the heart). In some embodiments, the fractional derivative of a fraction of a real number or a fraction of an integer number is applied numerically to the measured biopotential signals, or a portion thereof, in the frequency domain, to increase the dimensionality of the measured signal data. In some embodiments, the fractional derivative of an integer is applied numerically to the measured biopotential signals, or a portion thereof, in the frequency domain, to increase the dimensionality of the measured signal data. By mathematically modulating (e.g., by expanding or contracting) portions of a given biopotential signal, in the frequency domain, the numeric-based operation gives emphasis or de-emphasis to certain measured frequencies of the biopotential signals, which, when coupled with machine learning, facilitates improved diagnostics of certain pathologies and facilitates diagnostics in real-time (or near real time).

To this end, the exemplified method and system facilitates the measurements of biopotential signals using a single electrode lead to obtain diagnostics results. In addition, the exemplified method and system may be used to enhance measurements collected by multiple physical leads by, in effect, multiplying the physical effects with virtual lead that provide a different vantage point or perspective from the original physical measurement that improves the subsequent analysis.

A clinical animal model study was performed, the study illustrates that the exemplified method and system facilitates clinically-relevant diagnosis of physiologic conditions. In particular, the clinical animal model study illustrates that resolved congenital heart defects harboring hidden cardiovascular dysfunction can be detected using the exemplified method and system.

In an aspect, a method is disclosed of pre-processing data to extract variables for use in machine learning to diagnose a pathology. The method includes receiving a biopotential signal data associated with a subject, said biopotential signal data being associated with a biopotential signal collected from one or more electrical leads; generating, via a processor, a first and a second fractional derivative signal data by numerically performing one or more fractional derivative operations (e.g., a numeric fractional derivative operation) of the biopotential signal data in a frequency domain and converting a result of the one or more fractional derivative operations to a time domain signal data, wherein each of the first and second generated fractional derivative signal data comprises a same length and a same sampling frequency as the biopotential signal data; and generating, via the processor, a three-dimensional space wherein each corresponding value of the biopotential signal data, the first fractional derivative signal data, and the second fractional derivative signal data forms a three-dimensional point in said space, wherein geometric features and dynamical properties of the three-dimensional space are used as variables representative of the subject in machine learning to detect one or more diagnosable pathology of the subject.

In some embodiments, the first fractional derivative signal data is generated by performing a first numeric fractional derivative of a first order value on the biopotential signal data in the frequency domain and by performing an inversed transformation (e.g., inversed FFT) on the fractional derived signal data to convert the fractional derived signal data to a time domain signal data. In some embodiments, the inversed transformation comprises an inversed Fast Fourier Transform (inversed FFT) operation.

In some embodiments, the second fractional derivative signal data is generated by performing a second numeric fractional derivative of a second order value on the biopotential signal data in the frequency domain and by performing an inversed transformation (e.g., inversed FFT) on the fractional derived signal data to convert the fractional derived signal data to a time domain signal data.

In some embodiments, each of the first fractional derivative signal data and the second fractional derivative signal data comprises a time domain signal data.

In some embodiments, the first fractional derivative signal data is generated by a fractional derivative of an order of pi/2.

In some embodiments, the second fractional derivative signal data is generated by a fractional derivative of an order of 0.5.

In some embodiments, the geometric features and dynamical properties of the three-dimensional space are generated by performing a MMP (modified matching pursuit) algorithm of the three-dimensional point in said space.

In some embodiments, the biopotential signal data is associated with a biopotential signal collected from a single electrical lead.

In some embodiments, the single electrical lead collected measurements of the biopotential signal at a location selected from the group consisting of a chest line of the subject, a waistline of the subject, a wrist of the subject, a pelvic line of the subject, a neck of the subject, an ankle of the subject, a forehead of the subject, and an arm line of the subject.

In some embodiments, the method includes generating, via a processor, an alpha shape of the three-dimensional point in said space, wherein the geometric features and dynamical properties of the three-dimensional space includes the geometric features of the alpha shape.

In some embodiments, the method includes generating a Delaunay triangle mesh of the three-dimensional point in said space, wherein the geometric features and dynamical properties of the three-dimensional space includes the geometric features of the Delaunay triangle mesh.

In some embodiments, the biopotential signal data comprises electrocardiogram (ECG) data.

In some embodiments, the machine learning analysis comprises using an artificial neural network algorithm or a regression random forest algorithm.

In another aspect, a method is disclosed of pre-processing data to extract variables for use in machine learning to diagnose a pathology. The method includes receiving biopotential signal data associated with a subject, said biopotential signal data being associated with biopotential signals collected from two or more electrical leads; generating, via a processor, a fractional derivative signal data by numerically performing one or more fractional derivative operations of at least one of the biopotential signal data in a frequency domain and converting a result of the one or more fractional derivative operations to a time domain signal data, wherein the generated fractional derivative signal data comprises a same length and a same sampling frequency as the at least one of the biopotential signal data; and generating, via the processor, a three-dimensional space wherein each corresponding value of each of the biopotential signal data and the fractional derivative signal data forms a three-dimensional point in said space, wherein geometric features and dynamical properties of the three-dimensional space are used as variables representative of the subject in machine learning to detect one or more diagnosable pathology of the subject.

In some embodiments, each of the two or more electrical leads collected measurements of the biopotential signal at a location selected from the group consisting of a chest line of the subject, a waistline of the subject, a wrist of the subject, a pelvic line of the subject, a neck of the subject, an ankle of the subject, a forehead of the subject, and an arm line of the subject.

In another aspect, a method is disclosed of determining congenital heart defects (CHD) in a mammal. The method includes receiving biopotential recordings associated with the mammal, the biopotential recordings being recorded at predetermined intervals; developing variables associated with the biopotential recordings to create a dataset; and analyzing the dataset to determine if the mammal has a CHD.

In some embodiments, the biopotential recordings associated with the mammal are recorded using a measuring equipment comprising a single surface lead.

In some embodiments, a measuring equipment comprises an intracardiac electrogram instrument.

In some embodiments, the measuring equipment comprises a smart watch or fitness heart band.

In another aspect, a system is disclosed that includes that includes remote storage (e.g., storage area network) configured to receive biopotential data from a network-connected biopotential measuring apparatus; one or more processors; and a memory having instructions stored thereon, wherein the instructions, when executed by the processor, cause the processor to: generate phase space variables associated with the biopotential data; analyzing the phase space variables to determine if the mammal has a CHD.

BRIEF DESCRIPTION OF THE DRAWINGS

FIGS. 5A and 5B, is a detailed diagram of methods of virtual signal generation as shown in FIG. 3, in accordance with an illustrative embodiment.

DETAILED DESCRIPTION

Figure 1:
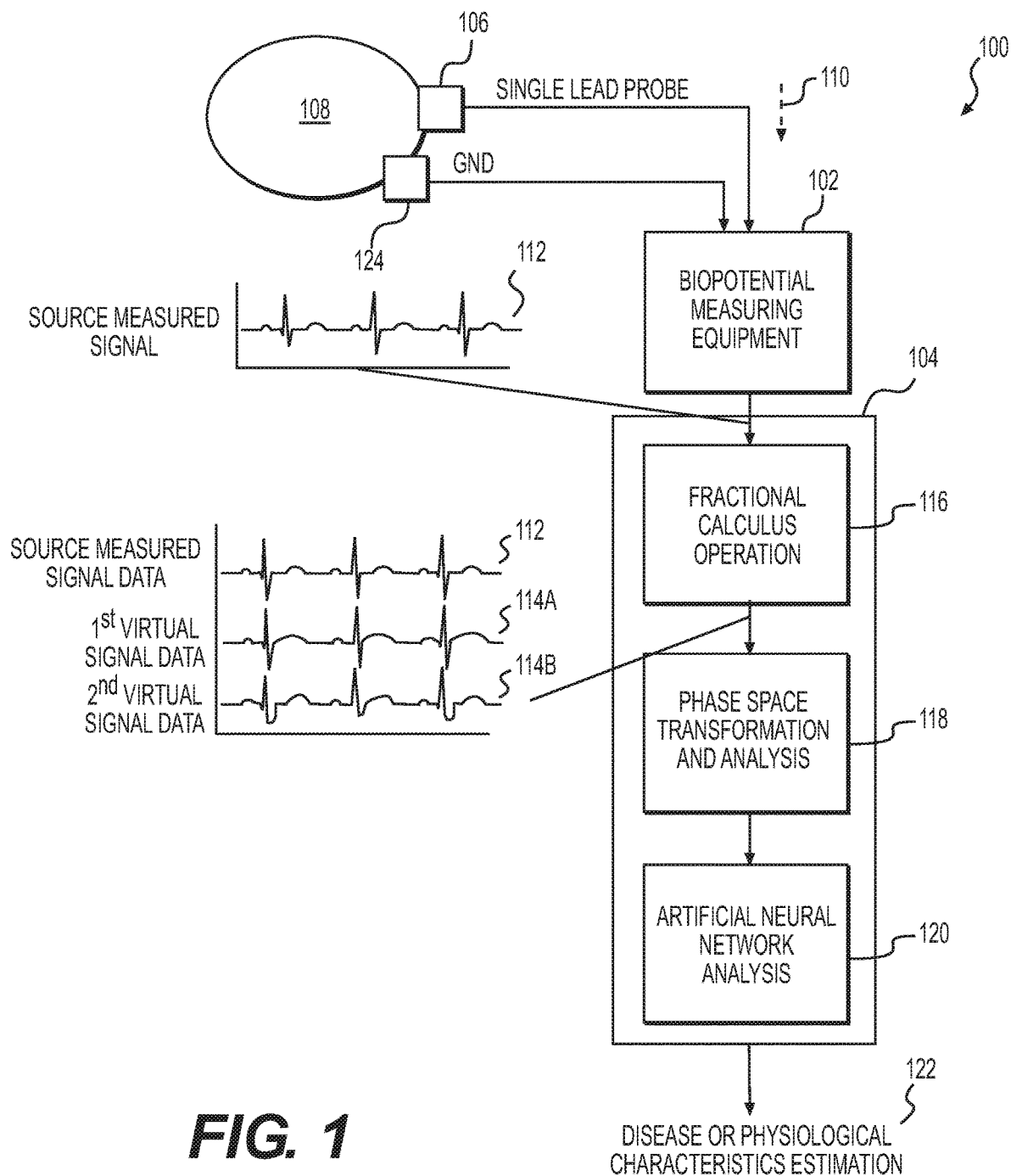
FIG. 1 is a diagram of a system for pre-processing data to extract variables for use in machine learning to diagnose a pathology, in accordance with an illustrative embodiment.

The components in the drawings are not necessarily to scale relative to each other and like reference numerals designate corresponding parts throughout the several views:

FIG. 1 is a diagram of a system 100 for pre-processing data to extract variables for use in machine learning to diagnose a pathology, in accordance with an illustrative embodiment. As shown in FIG. 1, the system 100 includes a biopotential measuring equipment 102 and an analysis subsystem 104. The biopotential measuring equipment 102 collects a biopotential signal via a single lead electrode 106 (and corresponding GND lead 124) that is attached to the surface of a subject 108 (e.g., the skin of a test animal or a person). The biopotential measuring equipment may be any device configured to capture electrophysiological signal. In some embodiments, a Holter ECG monitor is used as the biopotential measuring equipment 102 for measuring and recording the biopotential signal.

In some embodiments, the single lead electrode 106 comprise a surface electrode that is placed directly, or indirectly, on the surface of the skin or body tissue to record electrical activity. In some embodiments, the single lead electrode 106 comprises electrodes that are integrated into wearable devices to contact the skin when the wearable device is wore or attached to a patient or subject.

It should be appreciate that other wiring topology may be used without departing from the spirit of the disclosure. In some embodiments, the GND lead is a common-mode return. In other embodiments, the GND lead may serve as a differential mode signal with lead 106. In other embodiments, the GND lead is referenced to (or returned through) the earth, the chassis, or a shield.

Biopotential signals, in some embodiments, are electric potential that is measured between points on a tissue. Examples of biopotential signal includes an ECG (electrocardiogram) signal that is used to assess electrical and muscular functions of the heart.

In some embodiments, the biopotential measuring equipment is a wearable device that is configured to measure and to record the biopotential signal. In some embodiments, the wearable device is configured to be placed at a chest line of a subject, a waistline of the subject, a wrist of the subject, a pelvic line of the subject, a neck of the subject, an ankle of the subject, a forehead of the subject, and an arm line of the subject and has electrodes positioned to be in proximal contact with the skin or surface of the wearer. The wearable device may have a housing in the form of watch, an arm band, a neck band, a leg band, a chest band, a head band and such. In other embodiments, the biopotential measuring equipment is a part of an exercise equipment (e.g., a handle bar), a weight scale, a mat, or any like device that contacts the skin or surface of a person.

Referring still to FIG. 1, the biopotential signals 110 are stored as biopotential signal data 112. The analysis system 104 receives the biopotential signal data 112, in some embodiments, over a network, from the biopotential measuring equipment 102. In some embodiments, the analysis system 104 receives the biopotential signal data 112 from a storage area network (SAN). In other embodiments, the analysis system 104 and biopotential measuring equipment 102 are located a single device, e.g., a wearable device. Other configurations may be used.

Referring still to FIG. 1, the analysis system 104 is configured to generate, from the source biopotential signal data 112 of a single signal, one or more additional biopotential signal data (shown as a first fractional derivative signal data 114a and a second fractional derivative signal data), via a fractional calculus operation 116, of the source biopotential signal data 112, where each of the first and second generated fractional derivative signal data 114a, 114b comprises a same length and a same sampling frequency as the biopotential signal data. In some embodiments, the numerical fractional derivative operation is performed to emphasize or deemphasize certain frequency components and such that there is an absence of orthogonality in the resulting vectors. The additional biopotential signal data are used in conjunction with the source biopotential signal data to generate a phase space map to be used in subsequent phase space analysis 118 later described herein. The output of the phase space analysis are then evaluated using artificial neural networks 120 to assess parameters 122 associated with a presence of a disease or physiological characteristic. The output of the processor is then transmitted to a graphical user interface for visualization. The graphical user interface, in some embodiments, is included in a display unit configured to display parameters 122. In some embodiments, the graphical user interface displays intermediate parameters such as a 3D phase space plot representation of the biopotential signal data and virtual biopotential signal data.

Figure 2:
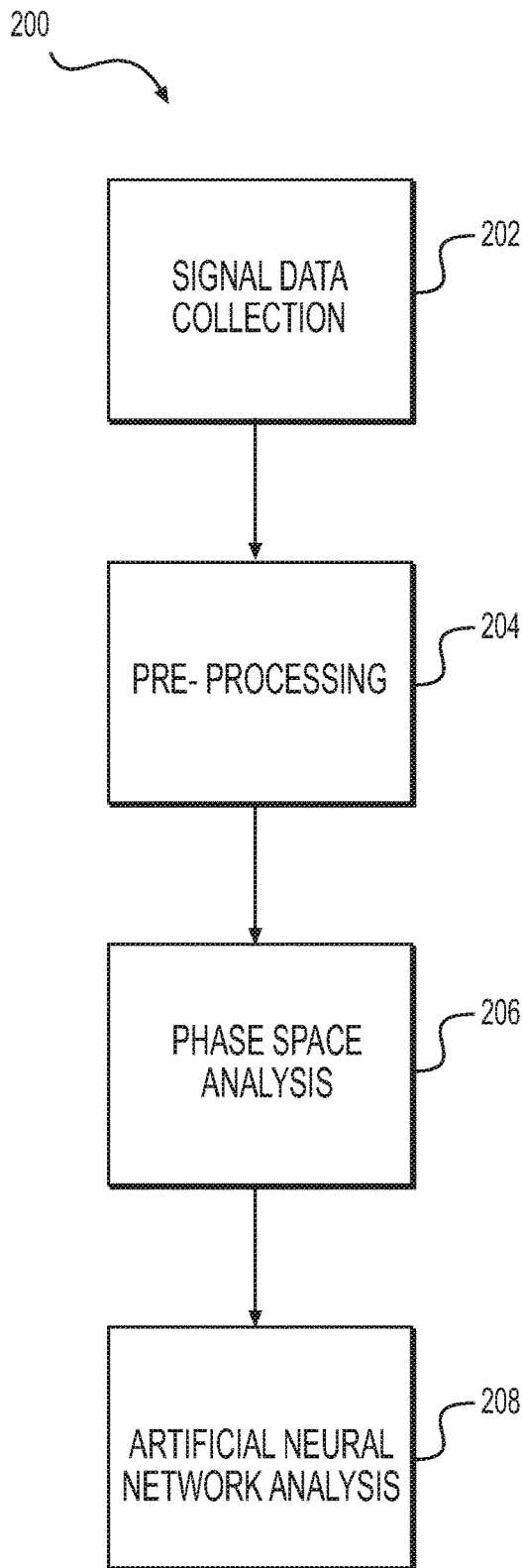
FIG. 2 is a diagram of a method for processing data to diagnose a pathology, in accordance with an illustrative embodiment.

FIG. 2 is a diagram of a method 200 of FIG. 1 for processing data to diagnose a pathology, in accordance with an illustrative embodiment. As shown in FIG. 2, the method 200 includes collecting 200 signal data and pre-processing 204 the signal data to generate a phase space dataset to be used in phase analysis 206, whereby features of the phase space dataset are extracted and evaluated via an artificial neural network analysis 208.

Figure 3:
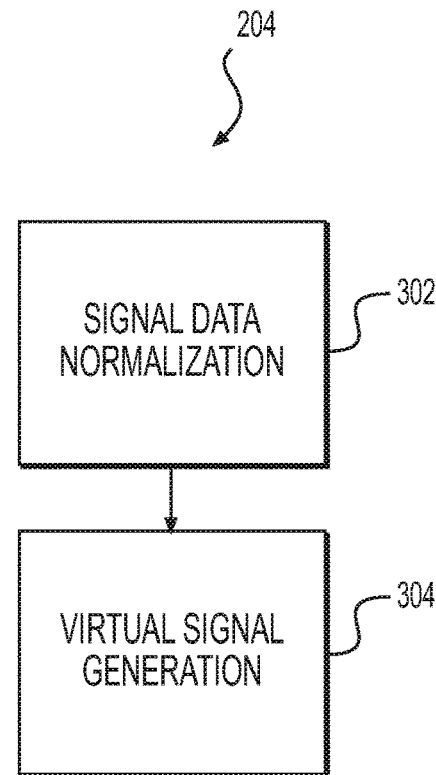
FIG. 3 is a detailed diagram of a method of pre-processing the data as shown in FIG. 2, in accordance with an illustrative embodiment.

FIG. 3 is a detailed diagram of the pre-processing 204 of the data as shown in FIG. 2, in accordance with an illustrative embodiment. The pre-processing 204 includes, in some embodiments, signal data normalization 302 and virtual signal generation 304.

Figure 4:
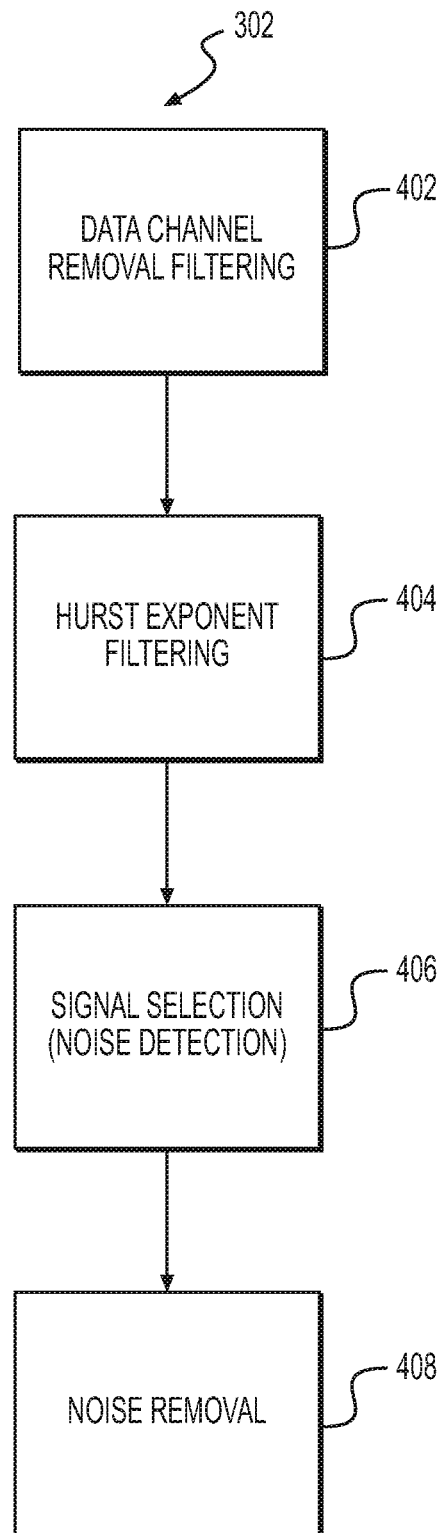
FIG. 4 is a detailed diagram of a method of signal data normalization as shown in FIG. 3, in accordance with an illustrative embodiment.

FIG. 4 is a detailed diagram of a method of signal data normalization as shown in FIG. 3, in accordance with an illustrative embodiment. As shown in FIG. 4, the signal normalization 302 includes an initial step of data channel removal 402 and Hurst exponent filtering 404 of the source biopotential signal data 112. Further detail of the data channel removal and Hurst exponent filtering is described in Matteo et al., "Scaling behaviors in differently developed markets," *Physica* A, 324, pg. 183-188 (2003). In some embodiments, the signal normalization 302 further includes selecting 406 a cleanest segment of the filtered signal, the segment having a minimized residue between a wavelet model, of the signal, that is designed to detect the presence of a non-biological noise and the signal itself. For example, a segment comprising a cleanest 5-second window of a 10 second recording interval may be selected. In some embodiments, the wavelet model is configured to decompose the signal into temporal levels in wherein one or more of the highest levels of decomposition of the temporal levels are used in the subtraction of the wavelet model from the signal to determine the residue. In some embodiments, the signal normalization 302 further includes filtering 408 using a second wavelet model to remove undesired noise (e.g., any remaining noise) in the selected cleaned segment. The second wavelet model is configured decompose the signal into a number of temporal levels and one or more of the highest level of decomposition are maintained. It should be appreciated by one skilled in that art that other signal data normalization may be used.

Figure 5:
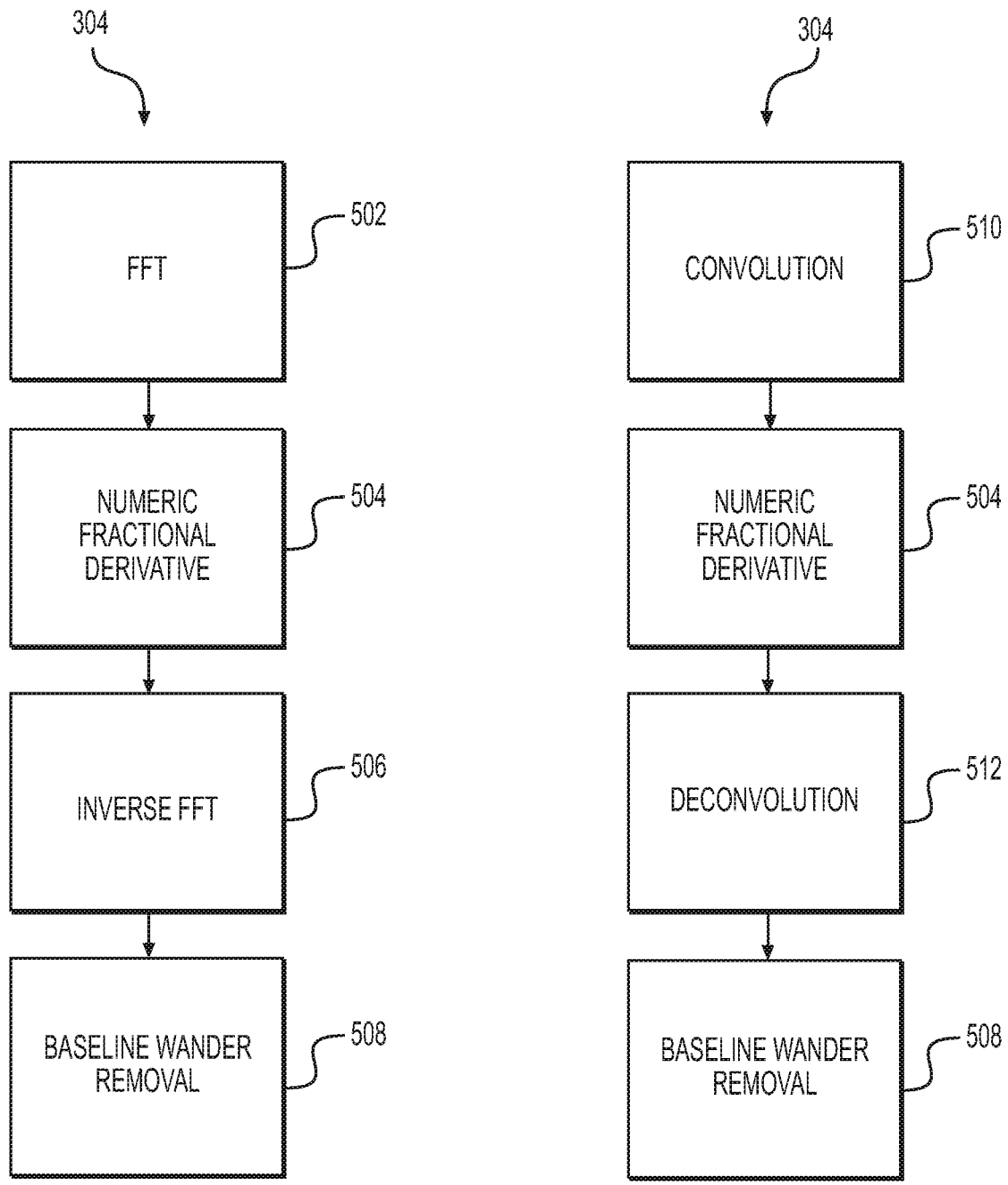
FIG. 5, comprising

FIG. 5 is a detailed diagram of a method of virtual signal generation as shown in FIG. 3, in accordance with an illustrative embodiment. As shown in FIG. 5, the virtual signal generation 304 includes creating one or more virtual signal data such that the data interact with the original signal data to create a valid phase space portrait in which the limit cycles of the input biopotential signal (e.g., cardiac cycle) are overlaid in 3-dimensional space and there was an absence of orthogonality in the resulting vector. For example, where a single source biopotential signal data is available, the virtual signal generation 304 may be used to generate two virtual biopotential signals where a valid phase space portrait is in 3 dimensional space. In another example, where two source biopotential signal data are available, the virtual signal generation 304 may be used to generate a virtual biopotential signal where a valid phase space portrait is in 3 dimensional space. In some embodiments, the valid phase space portrait may be in dimensional space greater than 3, such as 4, 5, 6, 7, 8, 9, 10, or greater.

In some embodiments, each of the one or more virtual signal data is generated by performing a Fast Fourier Transform 502 on the normalized signal data. A numerical fractional derivative is then performed 504 on each of the FFT signal data and an inversed Fast Fourier Transform (inversed FFT) is performed 506 on that output. Examples of the order of the fractional derivative include pi/2 or 0.5. In some embodiments, the order of the fractional derivative is a fraction of a real number or complex number. In some embodiments, the order of the fractional derivative is a fraction of an integer. In some embodiments, the output of the inversed FFT is further processed to remove 508 baseline wander.

In some embodiments, each of the one or more virtual signal data is generated by performing a numerical fractional differencing on the normalized signal data, implemented through the use of a convolution. A rational transfer function is defined to correspond to the specified order of the fractional derivative, which is then applied to the input data through the use of a digital filter configured to accept such input. Examples of the order of the fractional derivative include pi/2 or 0.5. In some embodiments, the order of the fractional derivative is a fraction of a real number or complex number. In some embodiments, the order of fractional derivative is a fraction of an integer. In some embodiments, the output of the convolution is further processed to remove 508 baseline wander.

Figure 6:
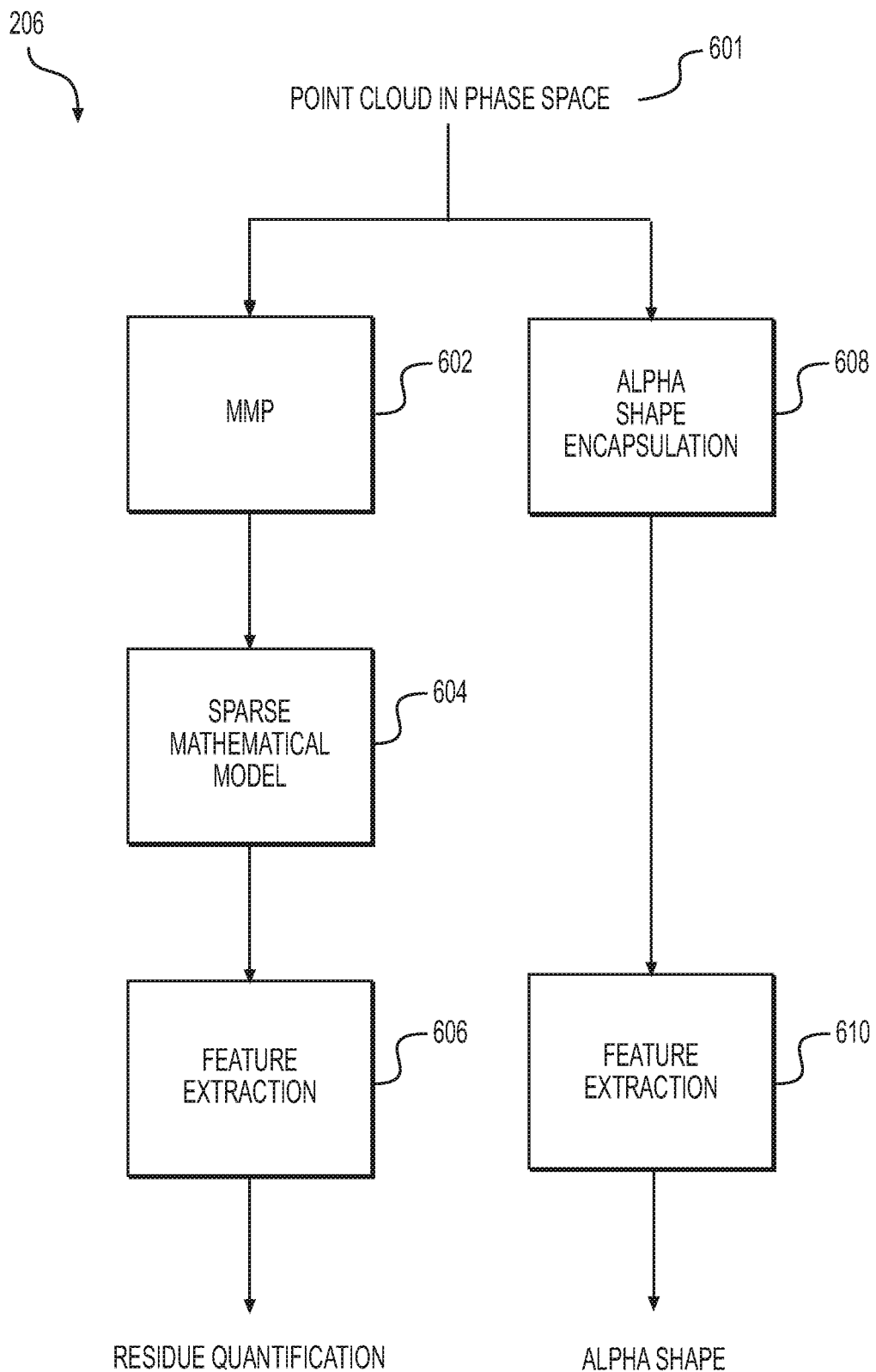
FIG. 6 is a detailed diagram of a method of performing phase space analysis as shown in FIG. 2, in accordance with an illustrative embodiment.

FIG. 6 is a detailed diagram of the method of performing phase space analysis as shown in FIG. 2, in accordance with an illustrative embodiment. In some embodiments, the input to the phase space analysis is a point-cloud phase space map 601 of the biopotential signal data and corresponding virtual signal data as a vectorcardiogram. In some embodiments, the phase space analysis includes performing modified matching pursuit (MMP) algorithm 602. The MPP algorithm 602 may be used to generate a sparse mathematical model 604. Detail of the MMP algorithm is provided in Mallat et al., "Matching Pursuits with Time-Frequency Dictionaries," IEEE Transactions on Signal Processing, Vol. 41 (12), Pages 3397-2415 (1993).

Characteristics of this model may be extracted, in a feature extraction operation 606, to determine geometric and dynamic properties of the model.

In some embodiments, the point-cloud phase space map 601 is encapsulated by alpha shape or a Delaunay triangulation. Features of the alpha shape and/or triangulation may be extracted, via feature extraction 610, to determine additional geometric and dynamic properties of the model.

In some embodiments, the extracted geometric and dynamic properties of the alpha shape and modified matching pursuit operations are use as variables to an artificial neural network analysis, a regression random forest analysis, or other machine learning analyses.

Experiment—Latent Teratogen-Induced Heart Deficits

Using an animal model described below, the exemplified system and method of using mathematical analysis and machine learning to diagnose disease is shown. Specifically, the exemplified system and method employs fractional calculus to increase the dimensionality of a single lead ECG via, a numerical method with the inverse FFT to be used in subsequent phase space analysis.

The exemplified system and method was shown to successfully extract meaningful variables from biopotential signals, in an animal model, specifically those from electrocardiogram data collected from an implanted radiotelemeter, at a time when teratogen-exposed test animals are clinically indistinguishable from controls. Machine learning was then leveraged to predict, within a robust validation framework, the presence of latent cardiovascular dysfunction. The test illustrates that the exemplified system and method can be used to analyze data (e.g., single time series data) from single lead measurements and to generate higher level of dimensional phase space data in a subsequent phase space analysis.

In the animal model, test rats were treated in such a way as to induce a high incidence of CHD (congenital heart defects) in offspring. Dams delivered naturally, and the heart structure and function were assessed in female pups using echocardiography on postnatal day (PND) 4, PND 21 and PND 56. At postnatal day (PND) 56, radiotelemetry units were implanted into 9 treated rats and 8 control rats. Two weeks post-surgery, telemeters were activated and ECG recordings were continuously collected every 10 seconds and every 12 seconds over a period of two weeks. 50,000 collected data points per rat were each transformed, from the single ECG recording, into a unique three-dimensional phase space dataset, and machine learning used to create predictive algorithms capable of identifying differences in heart function between control and treated rats and other mammals.

The results, as described in more detail below, demonstrate that a teratogen-induced CHD that resolves postnatally and results in hearts that appears normal by conventional measures are, in fact, different from teratogen-naïve hearts. As equally important, the results reveal that fractional calculus may be used to increase the dimensionality of a single lead biopotential signal for use in phase space analysis.

Experiment Setup

Figure 7:
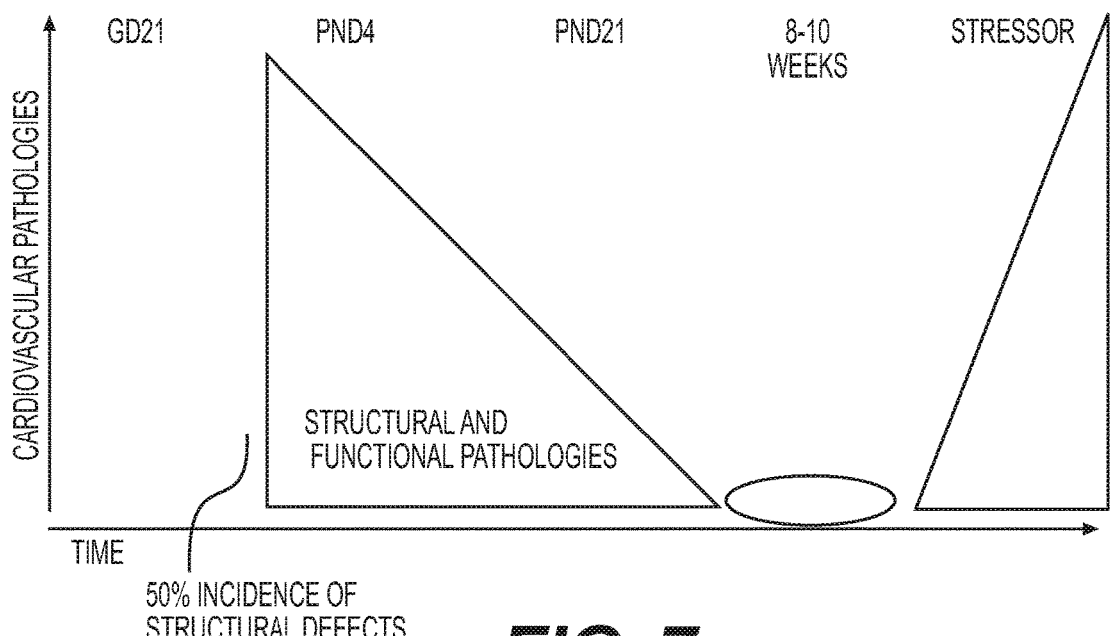
FIG. 7 is a diagram illustrating postnatal VSD resolution, in accordance with an illustrative embodiment, in accordance with an embodiment, in accordance with an embodiment.

FIG. 7 is a diagram illustrating postnatal ventricular septal defect (VSD) resolution, in accordance with an illustrative embodiment. As shown in FIG. 7, two cohorts of animals are selected with significant cardiovascular differences that decline to an absolute minimum at 8-10 weeks postnatal when these differences in the animals are clinically indistinguishable. The animals are used to verify that the exemplified system and method may be used to identify which animals were affected by drug administration (i.e., during this 8-10 week postnatal period when the cardiovascular differences in the animals are clinically indistinguishable).

Figure 8:
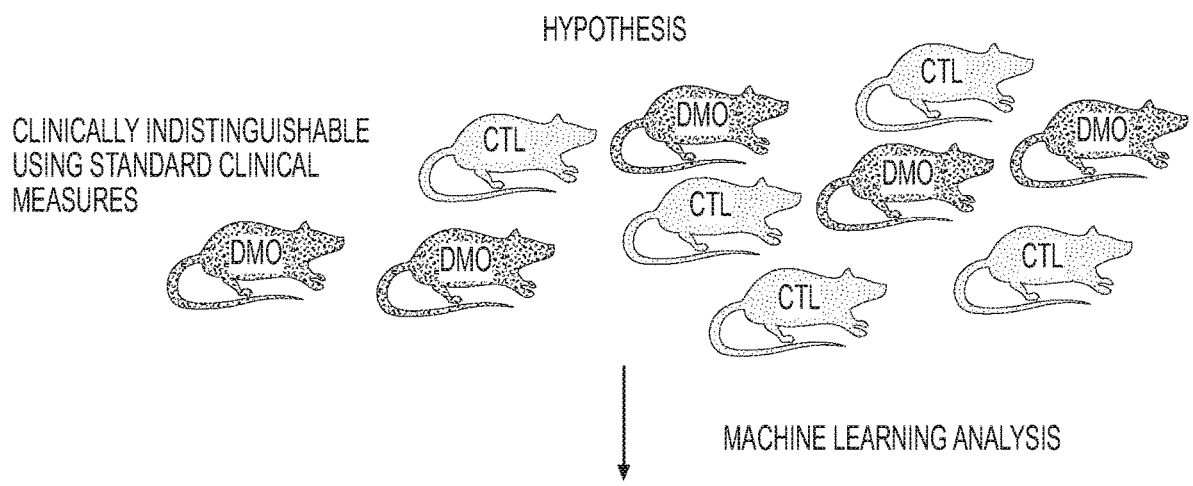
FIG. 8 is a diagram illustrating hypothesis of a clinical study, in accordance with an embodiment.

FIG. 8 is a diagram illustrating hypothesis of a clinical study, in accordance with an embodiment. As shown in FIG. 8, the hypothesis is that exemplified mathematical analysis and machine learning will reveal functional deficits between the cohort of offspring with treated dams and the cohort of offspring with non-treated dams at a time when it is otherwise undetectable by conventional analysis (during the 8-10 week period) without the need for a conventional stressor.

Figure 9:
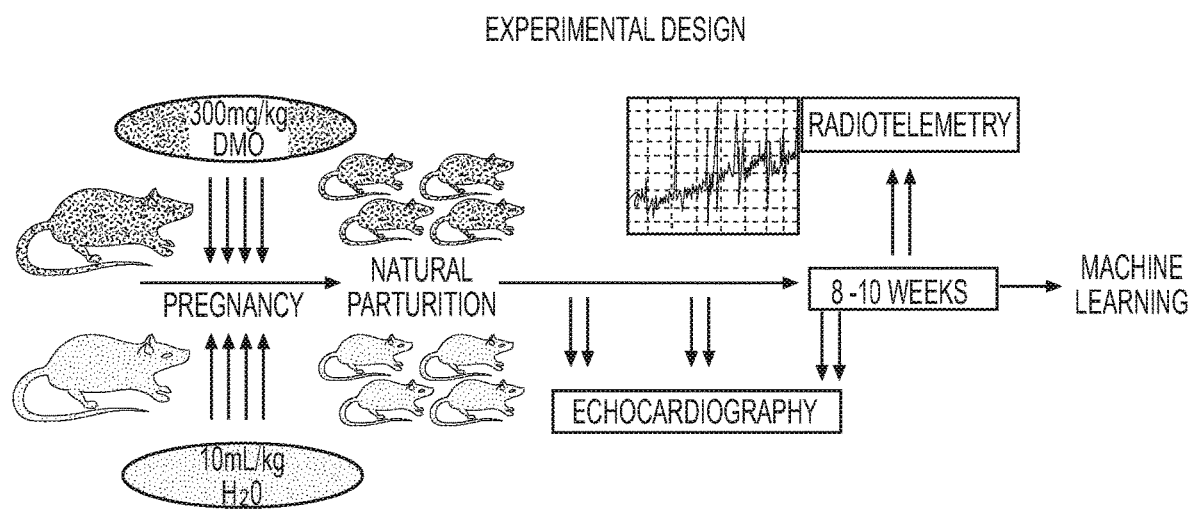
FIG. 9 is a diagram illustrating a design of experiment for the clinical study described in relation to FIG. 8, in accordance with an embodiment.

FIG. 9 is a diagram illustrating a design of experiment for the clinical study described in relation to FIG. 8, in accordance with an embodiment. As shown in FIG. 9, the test rats were divided into two cohorts: exposed and unexposed to dimethadione (DMO). The test rates were allowed to come to natural parturition; the pups were evaluated over the first 8 weeks of life using echocardiography. Then, at 8 weeks, radiotelemeters were surgically implanted into the test rats to measure several physiological signals including ECG signals. The ECG signals were then used in machine learning to create a predictor to discriminate between the two cohorts.

Figure 10:
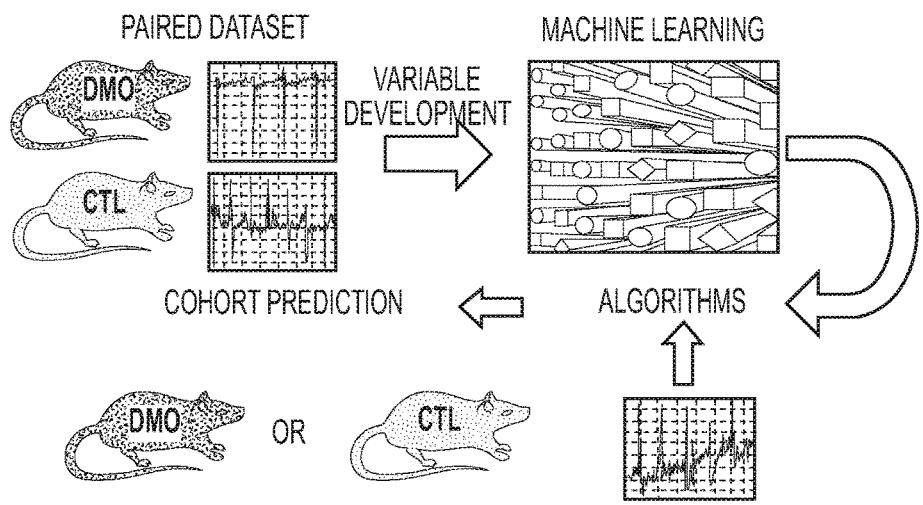
FIG. 10 is a diagram illustrating a method for conducting the experiment for the clinical study described in relation to FIG. 9 using machine learning process, in accordance with an embodiment.

FIG. 10 is a diagram illustrating a method for conducting the experiment for the clinical study described in relation to FIG. 9 using machine learning process, in accordance with an embodiment. As shown in FIG. 10, the exemplified experiment begins with test rats with known exposure paired to ECG data. Variables were then developed from the ECG data, and input to a machine learning process. The exemplified method and system is used to predict if the rat that generated that ECG was exposed or unexposed to dimethadione (DMO).

Figure 11:
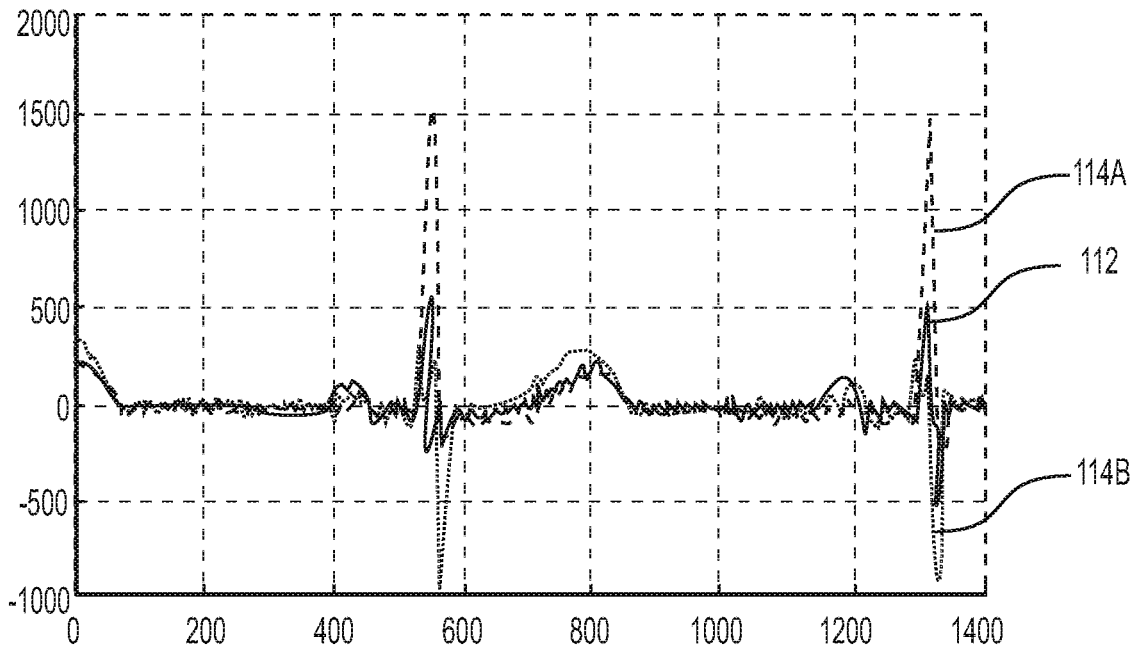
FIG. 11 is a diagram illustrating a vectorcardiogram including virtual biopotential signals generated from an exemplified fractional derivative operation, in accordance with an embodiment.

FIG. 11 is a diagram illustrating a vectorcardiogram including virtual biopotential signals generated from an exemplified fractional derivative operation, in accordance with an embodiment. As shown in FIG. 11, the exemplary inputs include the original measured ECG signal data 112 and the virtual ECG signal data 114a, 114b.

Figure 12:
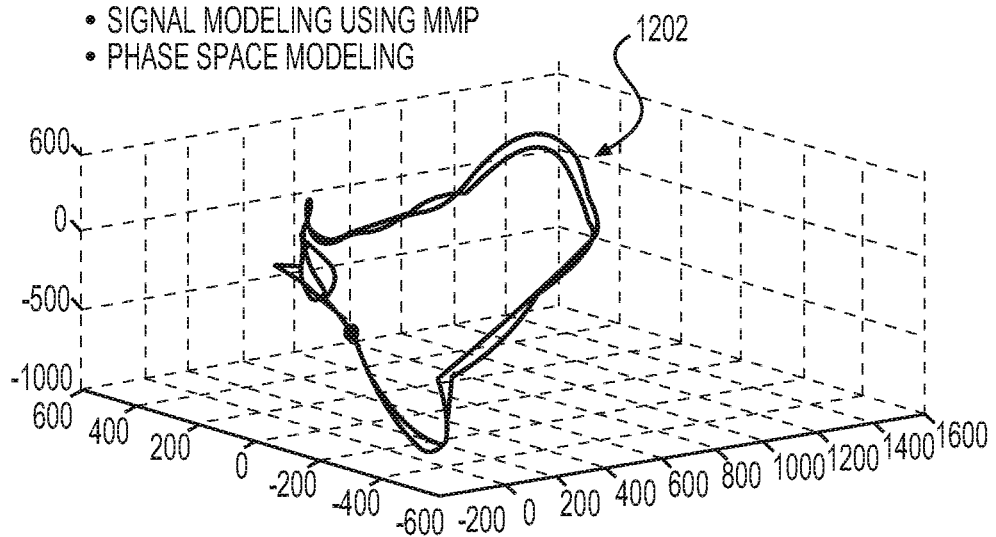
FIG. 12 is a diagram illustrating exemplary inputs to the machine learning processes described in relation to FIG. 10, in accordance with an embodiment.

FIG. 12 is a diagram illustrating exemplary inputs to the machine learning processes described in relation to FIG. 11, in accordance with an embodiment. As shown in the FIG. 12, a phase space dataset 1202 is shown of the vectorcardiogram (VCG) that includes the measured biopotential signals 112 and the virtual biopotential signals 114a, 114b generated from the exemplified fractional derivative operation. The vectorcardiogram (VCG) is shown in a point-cloud phase space map 1202 in which the measured biopotential signals 112 and the virtual biopotential signals 114a, 114b are shown without time in a three axis coordinate system. The phase space dataset 1202 is quantified by being wrapped in a geometric shape, for example, an alpha shape or a Delaunay triangle. Detail of an alpha shape operation is described in Edelsbrunner et al., "Three-dimensional alpha shapes," ACM Transactions on Graphics, Vol. 13 (1): 43-72 (1994).

Figure 13:
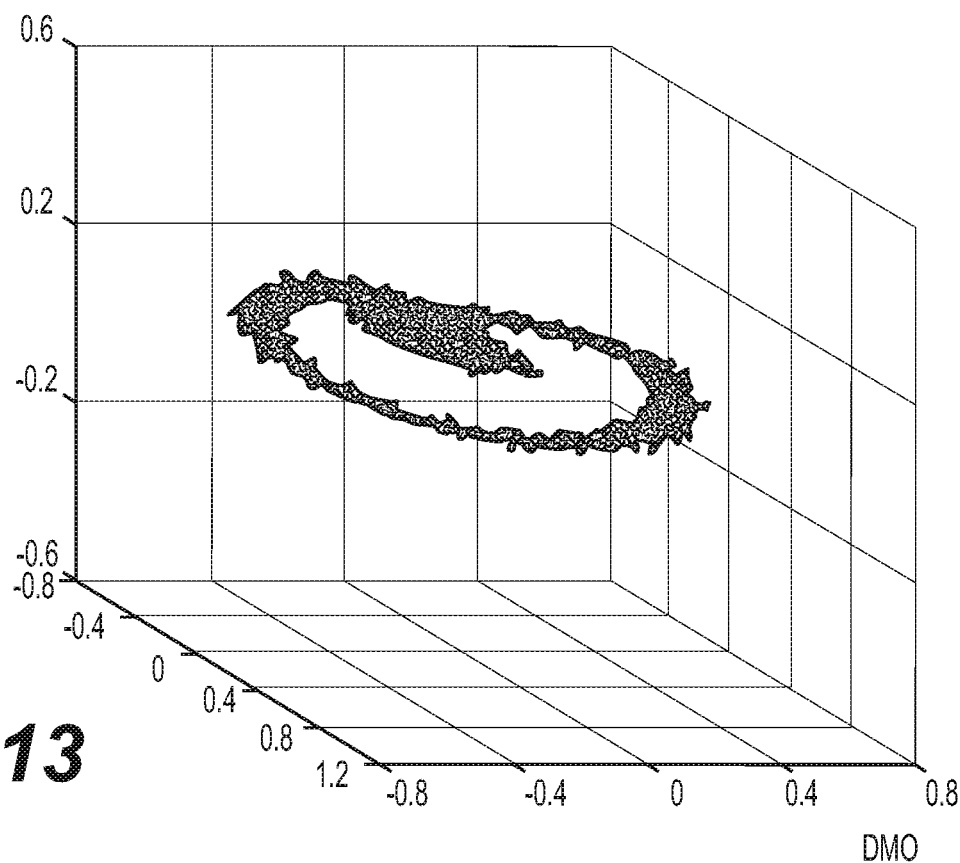
FIG. 13 is a diagram illustrating a phase space model of a vectorcardiogram of a specimen with a diagnosable disease.
Figure 14:
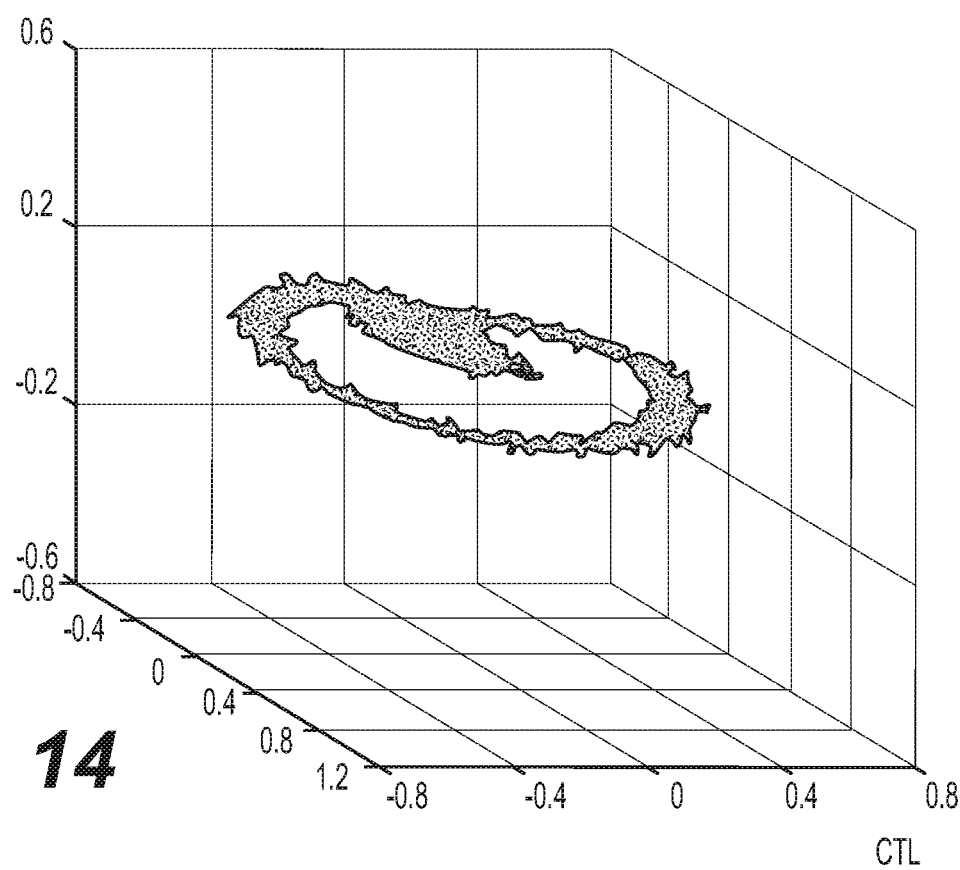
FIG. 14 is a diagram illustrating an alpha-shape phase space model of a vectorcardiogram of a control specimen.

FIG. 13 is a diagram illustrating an alpha-shape phase space model of a vectorcardiogram of a specimen with a diagnosable disease. FIG. 14 is a diagram illustrating an alpha-shape phase space model of a vectorcardiogram of a control specimen. As shown in FIGS. 13 and 14, there are visual differences between datasets of the exposed and unexposed test rats, but these differences are subtle and are more conducive to be analyzed via machine learning to expose such differences.

In some embodiments, the machine learning analysis uses families of variables including data shape variables, fractional derivatives, signal modeling using MMP, phase space modeling, and dynamical system variables. In the exemplified experiment, with data for 17 test rats, each with 50,000 ECG signals, where each ECG signal has 250 variables, there are about two billion data points used in the analysis including an artificial neural network.

Discussion

Congenital heart defects (CHD) are the most common class of congenital anomalies with an incidence of approximately 1.9-7.5% of live births. The most prevalent birth defect is the ventricular septal defect (VSD) at 25-40% of all CHD, in which the septum fails to close between the left and the right ventricles. Postnatal persistence or surgical repair of VSD or other CHD significantly increases the lifetime risk of heart disease in these patients relative to unaffected cohorts, and therefore necessitates a vigilant lifetime of observation and potential intervention by a cardiologist specializing in the care of CHD. Interestingly, approximately 80% of VSDs that present clinically resolve spontaneously within the first year of life. While a clinical resolution of the structural damage is a favorable outcome, there is a dearth of information about the long-term functional consequences of resolved VSD.

To explore the potential deleterious long-term consequences of resolved CHDs, the exemplified rat model was developed that recapitulates many of the clinical presentations of CHD. To generate such a model, pregnant rats were treated with a chemical teratogen. It has been estimated that 80% of in utero trimethadione exposures resulted in embryo/fetal loss, or malformations including a high incidence of CHD. Without wishing to be bound to particular theory, it is thought that DMO teratogenicity is mediated by oxidative stress which might be the result of the result of hypoxia reperfusion injury caused by bradycardias induced by disruption of calcium and potassium ion channels in embryonic myocytes. It has been demonstrated in outbred pregnant Sprague-Dawley rats that the incidence and severity of CHD in progeny are highly dependent upon the gestational window and total exposure to DMO. The administration of four 300 mg/kg doses every twelve hours beginning on the morning of gestation day (GD) 9 produces approximately a 50% incidence of CHD if fetuses are examined on GD 21, one day prior to natural parturition (see, e.g., Weston et al., "Co-variation in frequency and severity of cardiovascular and skeletal defects in Sprague-Dawley rats after maternal administration of dimethadione, the N-demethylated metabolite of trimethadione. Birth defects research Part B," Developmental and reproductive toxicology, Vol. 92, Pages 206-15 (2011)). When similarly treated dams are allowed to deliver their progeny naturally and the cardiac structure and function of the pups is evaluated longitudinally by high-resolution echocardiography, a scenario reminiscent of the clinical presentation of CHD is revealed. For example, in infants, approximately 80% of VSD resolves by one year of age, and in test rats after DMO exposure, about 80% of the VSD resolve spontaneously by weaning. Other structural elements such as left ventricular (LV) mass, LV anterior wall thickness in systole (LVAW;s) and LVAW in diastole (LVAW;d) are all significantly different between control and DMO-exposed pups close to the time of parturition, but resolve over time such that by 10 weeks of age control and DMO animals are indistinguishable. In the rat pups exposed to DMO, cardiac dysfunction is pronounced close to parturition, but gradually resolves, such that by 10 weeks of age under basal, during unstressed conditions, cardiac output (CO), stroke volume (SV), ejection fraction (EF), fractional shortening (FS) and pulmonary artery regurgitation PA regurg. (mm/s) have all normalized. At this point, radiotelemeters capable of measuring continuous single channel electrocardiogram (ECG) were surgically implanted into the rats. After two weeks of surgical recovery, baseline heart function was obtained and the animals were mated. Pregnancy is a physiological challenge for the maternal cardiovascular system and clinically has been referred to as a cardiovascular "stress test". Pregnancy-induced changes to the mammalian maternal CV system include a 30-40% increase in blood volume, 30-60% increase in cardiac output (CO), transient cardiac hypertrophy and uterine spiral arterial (SA) remodeling ref. Cardiac hypertrophy occurring in normal pregnancy is physiological and reversible, similar to exercise-induced hypertrophy.

Disconcertingly, the cardiovascular systems of test rats exposed to DMO in-utero adapted poorly to the burden of pregnancy. Manifestations included altered CO, SV, radial and longitudinal strain, and elevated mean arterial pressure at the time of spiral artery remodeling. Thus, the function of hearts with resolved CHD were indistinguishable from control hearts under basal unstressed conditions; however, under the stress of pregnancy profound cardiac and hemodynamic deficiencies emerged.

In the exemplified experiment, in-utero exposure to the heart teratogen DMO was used to generate a population of rats with resolved CHD that only presented with cardiac dysfunction during the burden of pregnancy. The exemplified method and system was used to predict the presence of latent teratogen-induced cardiac functional deficits prior to the onset of pregnancy, without the use of a cardiovascular stress test, and using the ECG data collected via the telemeter within the ten to twelve week period of the study previously described. There are no discernable differences between the cohorts during this ten to twelve week period.

Experiment Results

Figure 15:
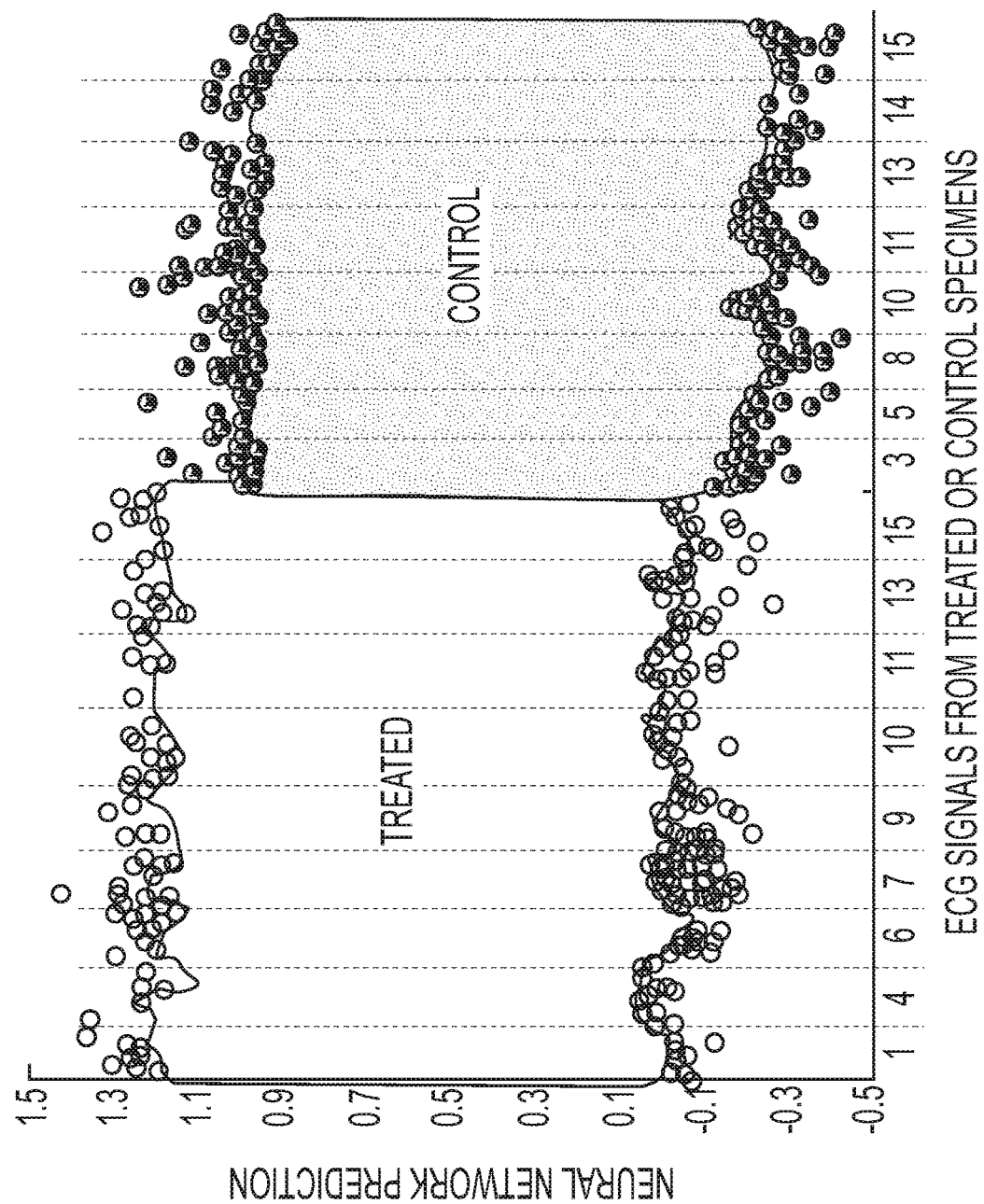
FIGS. 15 and 16 are diagrams illustrating results of the clinical study as described in relation to FIGS. 7-10, in accordance with an illustrative embodiment.
Figure 16:
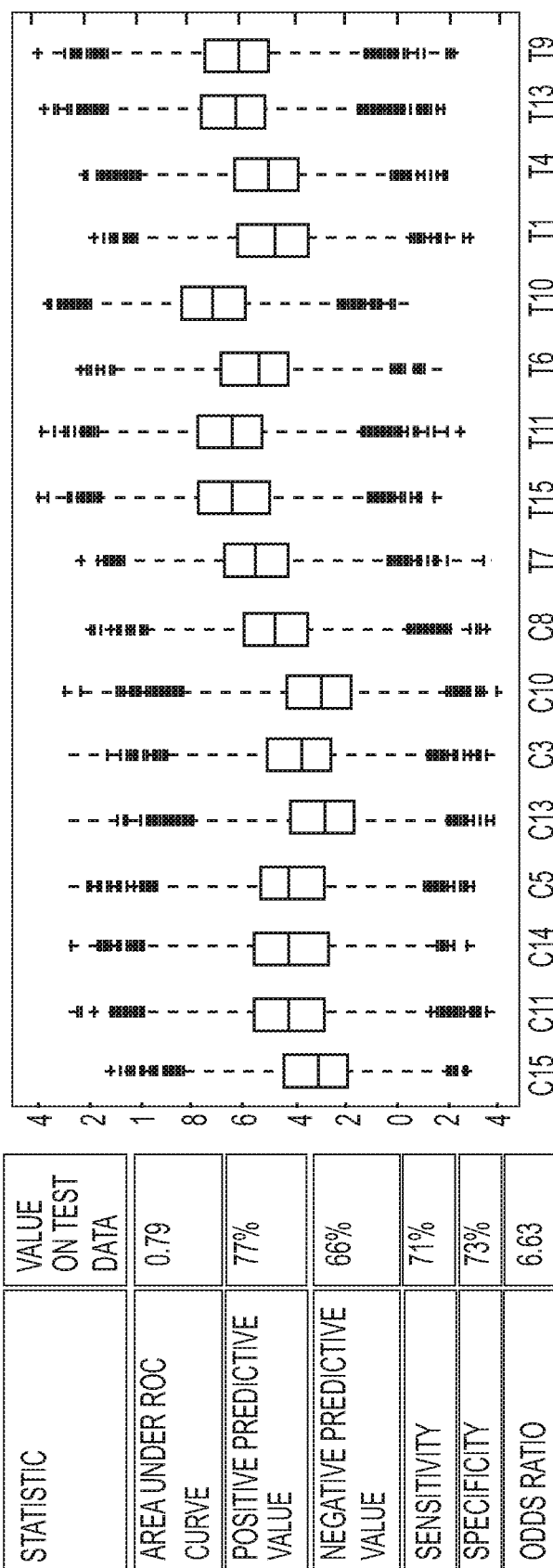

FIGS. 15 and 16 are diagrams illustrating results of the clinical study as described in relation to FIGS. 7-10, in accordance with an illustrative embodiment. Specifically, FIG. 15 is a plot of a predictive output of the neural network analysis for the two cohorts of test animals, which were by conventional measures, indistinguishable. The plot shows all the predictions on the treated and control cohorts test data (recall the 85%), where there is a clear visual separation between the baselines. For comparison, a heart-rate variability (HRV) analysis was run that uses landmarks in the ECG signal data to automatically detect high content data. As shown, HRV was not successful in identifying the cohorts, while the exemplified method and system (using the machine learning predictor) was found to be significantly better, showing that it is possible to discriminate between these two groups, and therefore they are different.

Specifically, the exemplified experiment was conducted with two cohorts in which five test rats were exposed to DMO in utero (Cohort #1), and eight control rats were chemical naïve (Cohort #2). Raw ECG signals were recorded from a single channel with a sampling frequency of 1000 Hz. Data acquisition was blocked into ten-second intervals from the test rats for a two week period between the ages of eleven to fourteen weeks, when the two cohorts were otherwise clinically indistinguishable using echocardiography or heart rate variability (HRV). The statistical evaluation of the predictors used to discriminate between the cohorts, such as HRV, primarily utilized area under the receiver operator characteristic curve (AUC). AUC examines the performance of a predictor against a binary target variable, which in this case, is the DMO-exposed or chemical naïve status of the rat. An AUC value of 0.5 represents a random prediction, an AUC of 1 is a perfect prediction, and an AUC of 0 is a perfect, but inverted, prediction (where all data points of one class are predicted to be the other class, and vice versa).

HRV reflects beat-to-beat changes in heart rate reflecting dynamic changes in autonomic tone. HRV is a clinically useful electrophysiological endpoint and is the foundation for risk stratification strategies such as REFINE, which seeks to determine whether non-invasive physiological parameters collected after the occurrence of a myocardial infarction (MI) predict the subsequent incidence of cardiac death or resuscitated cardiac arrest. In the REFINE study, HRV had an AUC of 0.62 and hazard ratio of 2.15 in the 10-14 week period post-MI, proving to be a somewhat useful technique for risk stratification, which led us to believe it might provide utility in the identification of DMO-exposed rats.

Figure 17A:
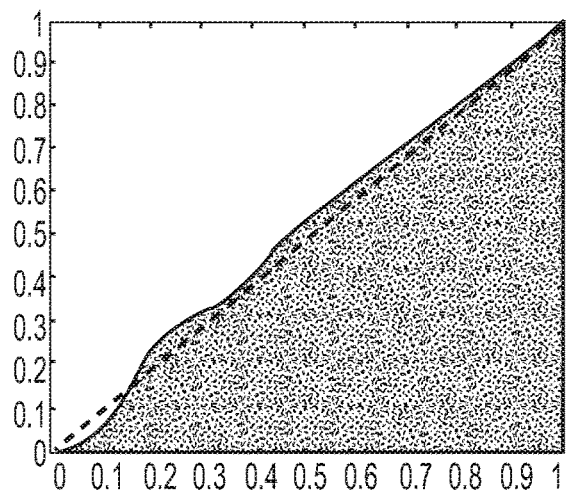
FIGS. 17A and 17B show the performance of heart rate variability as assessed using a receiver-operator characteristic curve in the prediction of DMO-exposed or chemical naïve status, using either the standard deviation method, or Poincare Pearson correlation method.
Figure 17B:
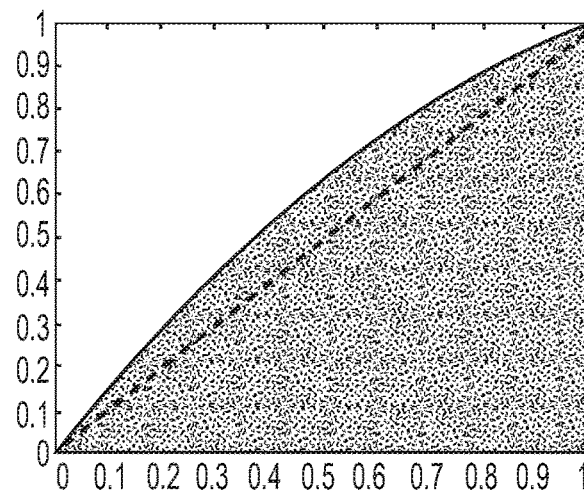

FIGS. 17A and 17B show the performance of heart rate variability as assessed using the receiver-operator characteristic curve in the prediction of DMO-exposed or chemical naïve status, using either the standard deviation method (FIG. 17A), or Poincare Pearson correlation method (FIG. 17B). FIGS. 17A and 17B were generated as follows. A five-second window that minimized non-biological noise was identified in a ten-second recording interval of a given test rat. Heartbeats were identified during this five-second window, and a confidence score (CS) determined; five-second windows possessing identified heartbeats with a CS greater than 0.7 were included in statistical evaluation. After heartbeat identification, HRV was calculated using the most widely accepted approach in which the standard deviation of the R-R interval (referencing the standard PQRST notation to represent the five waveforms in the cardiac cycle) was calculated for each five-second window. Additionally, a Poincaré plot was created in which the length of the R-R interval and the length of the next R-R interval create a point in two-dimensional scatter plot and the Pearson correlation of this data is calculated. The performance statistics of these two HRV techniques are reported in Table 1, with a threshold applied for statistics and the corresponding receiver operator characteristic curves are plotted in FIGS. 17A and 17B.

Table 1 shows statistical performance of heart rate variability in the prediction of DMO-exposed or chemical naïve status. The AUCs of these two predictors demonstrate that quantifying HRV using either method has low or no predictive power. The poor performance is additionally reflected in the diagnostic odds ratio (DOR), which is only slightly above 1 (where 1 indicates there is no change in the relative odds of the rat being DMO-exposed, given a positive test result).

TABLE 1

| Statistic | HRV: Standard Deviation | HRV: Poincare Pearson Correlation |
| --- | --- | --- |
| AUC | 0.51 | 0.59 |
| Sensitivity | 78% | 2% |

TABLE 1-continued

| Statistic | HRV: Standard Deviation | HRV: Poincare Pearson Correlation |
|---|---|---|
| Specificity | 23% | 99% |
| Positive Predictive Value | 39% | 48% |
| Negative Predictive Value | 62% | 62% |
| Diagnostic Odds Ratio | 1.05 (95% CI 1.03-1.07) | 1.47 (95% CI 1.37-1.58) |
| Number of rats correctly classified | 4/13 | 8/13 |
| Percent of intervals correctly classified | 44% | 61% |

Figure 18:
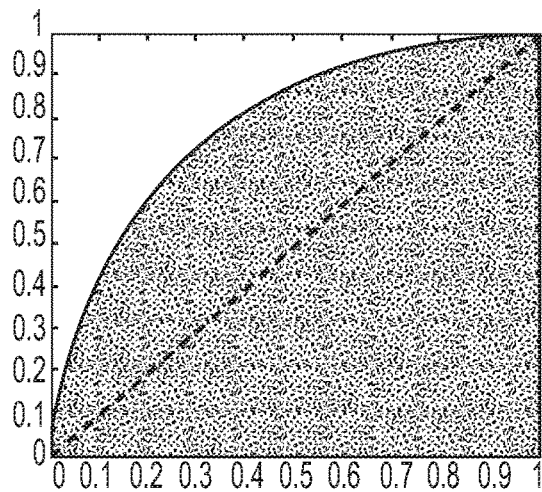
FIG. 18 show the performance of the artificial neural network on distinguishing the DMO-exposed data from the chemical naïve data as assessed using a receiver-operator characteristic curve.

FIG. 18 show the performance of the exemplified method suing artificial neural network on distinguishing the DMO-exposed data from the chemical naïve data, on the validation data when 15% of the data is allocated to the training set and the remaining 85% is allocated to validation set, as visualized by the receiver operator characteristic curve. In addition, Table 2 shows the statistical performance of the artificial neural network on distinguishing the DMO-exposed data from the chemical naïve data, on the validation data when 15% of the data is allocated to the training set and the remaining 85% is allocated to validation set.

TABLE 2

| Statistic | Value |
|---|---|
| AUC | 0.79 |
| Sensitivity | 70% |
| Specificity | 73% |
| Positive Predictive Value | 58% |
| Negative Predictive Value | 82% |
| Diagnostic Odds Ratio | 6.26 (95% CI 6.16-6.35) |
| Number of rats correctly classified | 12/13 |
| Number of intervals correctly classified | 72% |

ANNs are widely used in machine learning as they enable hitherto unachievable artificial intelligence benchmarks. A supervised ANN learns to predict a target using a vector of inputs in a way that mimics human neural processing. The ANN contains neurons arranged in a series of connected layers; firstly, the input layer that accepts the features, then one or more hidden layers to capture the non-linearity of the function being modeled, followed by the output layer that predicts the value of the target which corresponds to the input vector. The neurons in the ANN are stimulated by the input vector, and transmit those stimuli downstream to following layers depending on the value of the features, the strength of the connection between the neurons, and the activation function found within the neuron. ANNs may be used as a universal functional approximator.

To explore the possibility of creating a more robust prediction model, an ensemble machine-learning algorithm based on random forest was used which relies on the principle that a series of weak learners, or simple algorithms that describe a limited amount of complexity in the data, when used in combination have powerful generalization properties. Random forest is composed of decision trees as weak learners. Decision trees are tree structures where the nodes are decisions (or specific to this application, a threshold on a feature), and upon taking a decision the connection to that child node is followed, which reveals a sub-decision tree with the original child as the root. The process continues until arrival at a leaf node, which is the final prediction on the data. Each decision tree is exposed to a different partition of the both the recording intervals and the feature vector, and therefore tends to learn a distinct facet of the problem. A regression random forest algorithm with 100 decision trees was trained using the validation strategy just described, the results of which are shown in Table 3, and visualized in FIG. 19.

Figure 19:
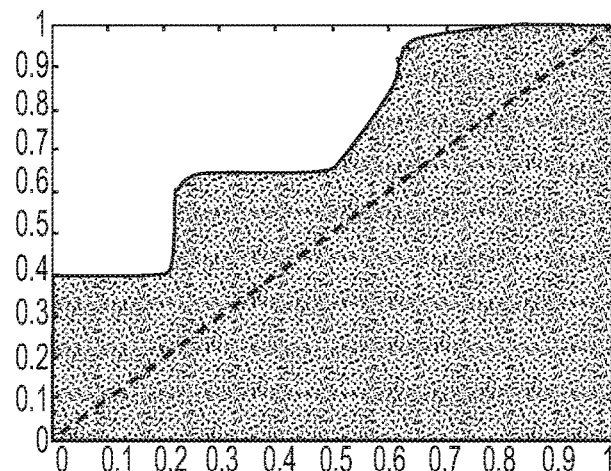
FIG. 19 shows the performance of the random forest on distinguishing the DMO-exposed data from the chemical naïve data within the "leave-one-out" validation paradigm, as assessed by a receiver operator characteristic curve.

FIG. 19 shows the performance of the random forest on distinguishing the DMO-exposed data from the chemical naïve data within the "leave-one-out" validation paradigm, as assessed by the receiver operator characteristic curve. As shown in FIG. 19, the performance is diminished slightly as compared to that of the first validation strategy as described in relation to FIG. 18, but in the context of this robust validation strategy it is still highly predictive. The performance is the result of analyzing the predictions produced in amalgamation by thirteen random forests (one for each of the thirteen test animals), each predicting on only the intervals of the single rat it did not receive in the training phase. The threshold, for those statistics requiring it, was set using the boundary that provided the maximal classification accuracy. When reserving a DMO-exposed rat for testing, the training set is composed of the 8 chemical naïve rats and the remaining 4 DMO-exposed rats, resulting in a ratio of 2:1.

Table 3 shows the statistical performance of the random forest on distinguishing the DMO-exposed data from the chemical naïve data within the "leave-one-out" validation paradigm.

TABLE 3

| Statistic | Random Forest |
|---|---|
| AUC | 0.73 |
| Sensitivity | 40% |
| Specificity | 99% |
| Positive Predictive Value | 97% |
| Negative Predictive Value | 70% |
| Diagnostic Odds Ratio | 80.4 (95% CI 77.0-84.0) |
| Number of rats correctly classified | 10 |
| Number of intervals correctly classified | 74% |

Experiment—Material and Methods

The analytical methodology described herein used pre-processing in the transition from data collection to feature extraction. Data channel removal and Hurst exponent filtering are the initial operations. The ideal threshold on which to accept data was observationally determined to be 0.7 on that exponent, which ranges from 0 to 1, through the visual inspection of a representative subset of the ECG signals along with the calculated exponents of those signals. Second, the cleanest 5-second window out of the 10-second recording interval was found by selecting the segment that minimizes the residue between a wavelet model of the signal, designed to detect the presence of non-biological noise, and the signal itself. The wavelet model is computed using the functionality of the MATLAB™ (MATHWORKS; Natick, Mass.) Wavelet Toolbox. Data outside of this 5-second segment is discarded.

In some embodiments, the filtering provides a clean signal that lend better to numerical operators (e.g., numerical fractional derivative operations). It should be appreciated by those skilled in the art that other filtering and signal cleaning operations may be used.

Following this, any remaining noise in this 5-second interval is removed using a second wavelet model, which is designed for noise removal rather than noise detection, but is otherwise similar to the model used for the selection of the 5-second segment. Both of the wavelet models decompose the signal into eight temporal levels, but the noise detection model only preserves the two highest levels of decomposition (resulting in efficient capture of noise when subtracting the wavelet model from the signal), while the noise removal model at least partially maintains the four highest levels of decomposition. The phase space reconstruction, and therefore the creation of the vVCG, was then performed through the creation of the two virtual signals. Transformations to create the two virtual signals were chosen such that the signals interact with the original signal to create a valid phase space portrait, where the limit cycles of the cardiac cycles were overlaid in 3-dimensional space and there was an absence of orthogonality in the resulting vectors. These virtual leads were created by taking derivatives of the acquired lead in such a way as to create a valid phase space portrait, or a shape in three-dimensional space where the values of each of the three leads at a given time form a three-dimensional point in that space. Fractional derivatives of order pi/2 and 0.5 were found to be suitable, as computed numerically through the conversion of the signal into the frequency domain using the Fast Fourier Transform (FFT), calculation of the required derivative within the frequency domain, and conversion of the derivative back to the time domain using the inverse FFT. The baseline wander was then extracted from each of the three dimensions through the use of a median filter with an order of 1500 ms, smoothed with a 1-Hz low-pass ideal filter, and subtracted from the signals. The bias was then removed from the resulting signals by subtracting estimations of the modes of the signals using the maximums of the probability densities calculated with a kernel smoothing function. Finally, all signals were divided by their interquartile ranges to complete the normalization process.

The three-dimensional space construction is subsequently used to study geometrical and dynamical properties of the system. The pre-processed signal is subjected to a feature extraction process. The signal is modeled with the modified matching pursuit (MMP) algorithm to create a sparse mathematical model. Characteristics of the model, including residue quantification, were included in the feature set. The vVCG was further quantified by creating an encapsulating alpha shape, or a specific Delaunay triangulation. This triangulation has associated characteristics that composed the feature vector representing the recording interval.

Delaunay triangulations are triangulations on a set of points such that no point is within the circumcircle of any triangle in the triangulation, and the minimum angle of all the angles in each triangle in the triangulation is maximized.

An alpha shape adds a further constraint; this triangulation requires the specification of an alpha radius, and only pairs of points whose distance is less than the alpha radius may be connected by an edge. The alpha radius in this feature extraction process was determined observationally to be 0.6, which allowed for sufficient encapsulation of the vVCG while still creating appropriate sparsity in the triangulation in areas of reduced point density.

This feature extraction was performed using SHARCNET (a consortium of colleges, universities and research institutes operating a network of high-performance computer clusters across southwestern, central and northern Ontario, Canada).

At the conclusion of the feature creation process, there were 250 features to represent the 10-second recording interval.

After the feature extraction, the ANN and random forest algorithms were invoked to create the predictors. An ANN was trained using the labeled feature vectors from 15% of the recording intervals, where the relatively small training percentage was chosen to minimize the potential to overfit and allow for generalizability. Selecting a relatively small segment of the available data for training, and performing well on the larger test set, requires that the ANN leverage overarching signatures in the data rather than patterns unique to the training set. The ANN had an input dimensionality of 250 neurons, a single hidden layer that expanded that dimensionality by a factor of three to a total of 750 neurons, and then a single neuron in the output layer to represent the prediction of DMO-exposed or chemical naïve. Each neuron in the ANN contained the hyperbolic tangent activation function. The ANN sought to minimize the root mean squared error between the prediction and the recording interval class on the training data using stochastic gradient descent. Low learning rate and momentum parameters were used to allow the ANN to evolve gradually, and input corruption (the addition of noise on the incoming features) as well as dropout (noise internal to the ANN) were used to control for overfitting, which occurs when the ANN is highly specific to the training data and is unlikely to generalize to novel data. The ANN was a custom implementation in the MATLAB language. The performance of this ANN when it was applied to the withheld 85% of the data (351,520 data points in total) is shown below in Table 2, and the corresponding ROC curve is plotted in FIG. 18.

With respect to the random forest, the MATLAB function TreeBagger was used in which the specification of the number of features to sample at each node in the tree was selected from all the features, thereby exploiting the varying levels of information present within the features, and yet gain the generalization benefit from the random sampling of the training data for each member of the random forest.

Heart rate variability was also calculated on the pre-processed signals. The detection of the R peaks was performed through the identification of high-confidence R peaks, or those that exist in the top decile of the signal, and the creation of templates based on these high-confidence peaks. A template matching procedure was then executed on the signal, identifying the peaks of segments of the signal with a high degree of similarity to the templates, resulting in an expanded set of R peaks. The confidence of these R peaks was then quantified by calculating the absolute difference between the maximum R-R interval and the minimum R-R interval, and dividing by the maximum R-R interval in order to create a normalized peak confidence score. The threshold on the score was set to 0.7 (not to be confused with the generalized Hurst exponent threshold, also set to 0.7), in order to allow for the heart rate variability that is to be expected in any mammalian cardiovascular system, yet remove any peak detections that are likely to have missed a peak or identified an additional peak, and thus depressing the confidence score. HRV can then be calculated on R-R intervals derived from the identified peaks, using the methods already described.

Although the invention is described in terms of particular embodiments and applications, one of ordinary skill in the art, in light of this teaching, can generate additional embodiments and modifications without departing from the spirit of or exceeding the scope of the exampled invention. Accordingly, it is understood that the drawings and descriptions herein are proffered by way of example to facilitate comprehension of the invention and should not be construed to limit the scope thereof.

For example, in view of the exemplified method and system, a single electrode lead measurements may be used in analysis that conventionally use data from multiple lead measurements, e.g., to assess certain physiologic characteristics or disease.

In addition, if the current observations in rat are clinically translatable, there are important implications with respect to the long-term cardiac health after spontaneous post-partum resolution of CHD. For example, the ability to identify latent markers of future cardiac dysfunction using only ECG signals would be a significant cost-effective step forward for the identification of at-risk individuals who typically do not outwardly display an inherent cardiac risk.

In addition, the animal model upon which these exemplified experiments are based, demonstrate that there are important implications with respect to the long-term cardiac health after spontaneous post-partum resolution of CHD.

What is claimed is:

1. A system for detecting one or more pathologies of a human subject, comprising:
   an analysis system configured with computer-readable instructions to retrieve an electrophysiological signal data set that (i) is associated with the subject and (ii) has been acquired by measuring equipment configured to non-invasively capture the signal data set via one or more sensors, the analysis system using the signal data set to detect the one or more pathologies of the human subject,
   wherein the detecting the one or more pathologies comprises:
      generating, by a processor executing a transformation operation, an intermediate data set from the signal data set, wherein the intermediate data set comprises an encapsulating alpha shape or a Delaunay triangle mesh data object of the signal data set; and
      generating, by the processor, one or more geometric features and/or dynamical properties of the alpha shape or the Delaunay triangle mesh, and
   wherein the generated one or more geometric features and/or dynamical properties of the alpha shape or the Delaunay triangle mesh are used as variables representative of the human subject in a machine learning operation to detect the one or more pathologies of the human subject.

2. The system of claim 1, wherein the intermediate data set is generated by:
   generating, by the processor, a reconstructed model of the signal data set, wherein the alpha shape or a Delaunay triangle mesh data object is generated from the reconstructed model.

3. The system of claim 1, wherein the signal data set includes cardiac data acquired from two or more channels, each of a biopotential signal acquired over a plurality of heart beats.

4. The system of claim 3, wherein the signal data set is acquired over a period of at least 10 seconds.

5. The system of claim 1, wherein the one or more sensors comprises an electrode.

6. The system of claim 1, wherein the machine learning operation comprises an artificial neural network algorithm or a regression random forest algorithm.

7. The system of claim 1, wherein the measuring equipment is configured to transmit the signal data set over a network to the analysis system.

8. The system of claim 1, wherein the one or more sensors are integrated into a wearable device configured to contact the skin when the wearable device is worn by or attached to the human subject.

9. The system of claim 1, wherein the measuring equipment comprises exercise equipment, a weight scale, or a mat.

10. The system of claim 1, further comprising:
    a storage area network, wherein the measuring equipment is configured to transmit the signal data set over a network to the storage area network, and wherein the analysis system is configured to retrieve the acquired signal data set from the storage area network for analysis.

11. A method comprising:
    retrieving, by a processor, from a storage area network, an electrophysiological signal data set that (i) is associated with a human subject and (ii) has been acquired by measuring equipment configured to non-invasively capture the signal data set via one or more sensors; and
    detecting one or more pathologies of the human subject using the signal data set, wherein the detection operation comprises:
       generating, by the processor executing a transformation operation, an intermediate data set from the signal data set, wherein the intermediate data set comprises an encapsulating alpha shape or a Delaunay triangle mesh data object of the signal data set; and
       generating, by the processor, one or more geometric features and/or dynamical properties of the alpha shape or the Delaunay triangle mesh,
    wherein the generated geometric features and/or dynamical properties of the alpha shape or the Delaunay triangle mesh are used as variables representative of the human subject in a machine learning operation to detect the one or more pathologies of the human subject.

12. The method of claim 11, wherein the intermediate data set is generated by:
    generating, by the processor, a reconstructed model of the signal data set, wherein the alpha shape or a Delaunay triangle mesh data object is generated from the reconstructed model.

13. The method of claim 11, wherein the signal data set includes cardiac data acquired from two or more channels each of a biopotential signal acquired over a plurality of heart beats.

14. The method of claim 13, wherein the electrophysiological signal data set is acquired over a period of at least 10 seconds.

15. The method of claim 11, wherein the one or more sensors comprises an electrode.

16. The method of claim 11, wherein the machine learning operation comprises an artificial neural network algorithm or a regression random forest algorithm.

17. The method of claim 11, wherein the measuring equipment is configured to transmit the signal data set over a network to an analysis system.

18. The method of claim 11, further comprising:
    transmitting, by the processor, the signal data set over the network to the storage area network, and wherein an analysis system is configured to retrieve the acquired signal data set from the storage area network for analysis.

19. A non-transitory computer readable medium having instructions stored thereon, wherein execution of the instructions by a processor cause the processor to:

retrieve from a storage area network, an electrophysiological signal data set that (i) is associated with a human subject and (ii) has been acquired by measuring equipment configured to non-invasively capture the signal data set via one or more sensors; and detect one or more pathologies of the subject using the signal data set by:

generating, by a transformation operation, an intermediate data set from the signal data set, wherein the intermediate data set comprises an encapsulating alpha shape or a Delaunay triangle mesh data object of the signal data set; and generating one or more geometric features and/or dynamical properties of the alpha shape or the Delaunay triangle mesh, wherein the generated geometric features and/or dynamical properties of the alpha shape or the Delaunay triangle mesh are used as variables representative of the human subject in a machine learning operation to detect the one or more pathologies of the human subject.

20. The computer-readable medium of claim 19, wherein the intermediate data set is generated by:

generating, by the processor, a reconstructed model of the signal data set, wherein the alpha shape or a Delaunay triangle mesh data object is generated from the reconstructed model.

* * * * *